United States Patent [19]
Kell

[11] Patent Number: 5,908,788
[45] Date of Patent: *Jun. 1, 1999

[54] METHOD OF MONITORING PATIENT COMPLIANCE WITH MEDICATIONS PRESCRIPTIONS

[75] Inventor: Michael Kell, Atlanta, Ga.

[73] Assignee: U.D. Testing, Inc., Gainesville, Ga.

[ * ] Notice: This patent is subject to a terminal disclaimer.

[21] Appl. No.: 08/697,063

[22] Filed: Aug. 19, 1996

Related U.S. Application Data

[63] Continuation of application No. 08/248,102, May 24, 1994, Pat. No. 5,547,878, which is a continuation-in-part of application No. 08/145,821, Nov. 2, 1993.

[51] Int. Cl.$^6$ .................................................. G01N 33/48
[52] U.S. Cl. .......................... 436/111; 436/171; 436/808; 436/901
[58] Field of Search ............................. 436/63, 111, 171, 436/808, 901

[56] References Cited

U.S. PATENT DOCUMENTS

| | | |
|---|---|---|
| 2,564,247 | 8/1951 | Carson et al. . |
| 3,856,469 | 12/1974 | Schneider et al. ...................... 234/230 |
| 3,901,655 | 8/1975 | Shukla et al. . |
| 4,104,367 | 8/1978 | Gomez et al. ................. 424/1 |
| 4,196,185 | 4/1980 | Focella et al. ............... 424/1 |
| 5,047,329 | 9/1991 | Suzuki ....................... 435/18 |
| 5,137,692 | 8/1992 | Fritz ......................... 422/61 |
| 5,179,027 | 1/1993 | Fisher ........................ 436/56 |
| 5,547,878 | 8/1996 | Kell ......................... 436/111 |

OTHER PUBLICATIONS

Balabanova, et al Methadone distribution in blood, cerebrospinal fluid, urine and organ tissues EMBASE No. 92091431 Austria 1991.

Nilsson et al Effect of Urinary pH on the disposition of methadone in man EMBASE No. 82171209 W. Germany 1982.

*Primary Examiner*—Lyle A. Alexander
*Attorney, Agent, or Firm*—Kennedy,Davis & Kennedy,P.C.

[57] ABSTRACT

A method of monitoring compliance of a patient that has been placed on a medication maintenance program with a prescribed medication dosage by determining a normalized urine methadone concentration. An unadulterated urine sample is obtained from the patient. The urine methadone concentration and urine specific gravity are measured. The normalized urine medication concentration is calculated as a function of the measured medication concentration in the urine and the urine specific gravity. The calculated normalized urine medication concentration is compared with an expected medication concentration value for the patient for the maintenance program prescribed to determine any significant differences therebetween as an indication of noncompliance. Alternatively, a urinary-parameter normalized urine medication concentration is calculated as a function of the measured medication concentration in the urine, the urine specific gravity and at least one selected pharmacokinetic parameter of the medication. The calculated urinary-parameter normalized urine medication concentration is compared with an expected medication concentration value for an average compliant patient for the maintenance program prescribed to determine any significant differences therebetween as an indication of noncompliance.

8 Claims, 8 Drawing Sheets

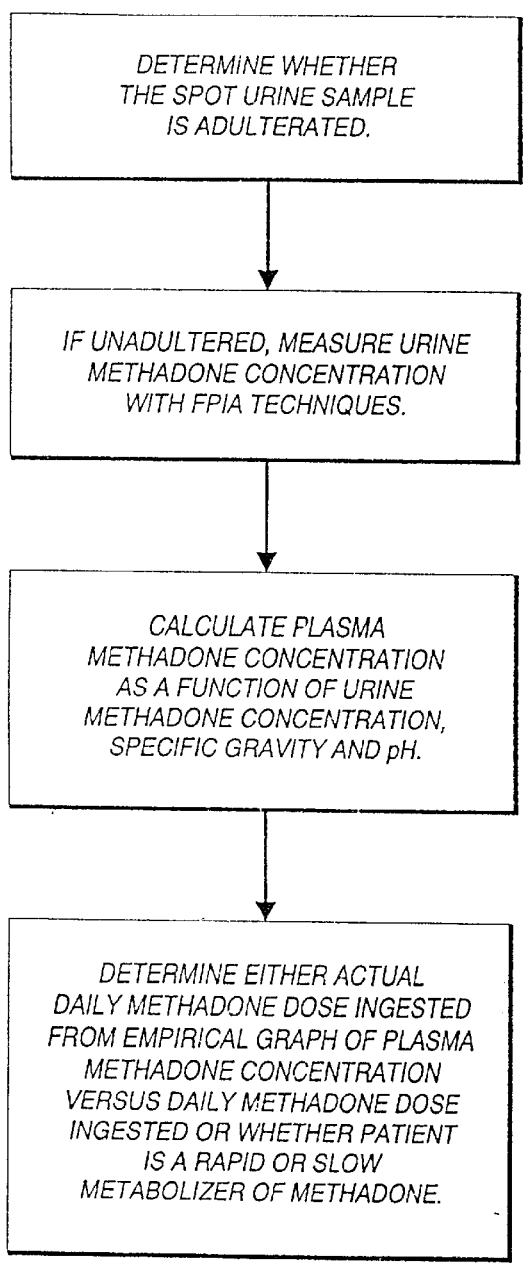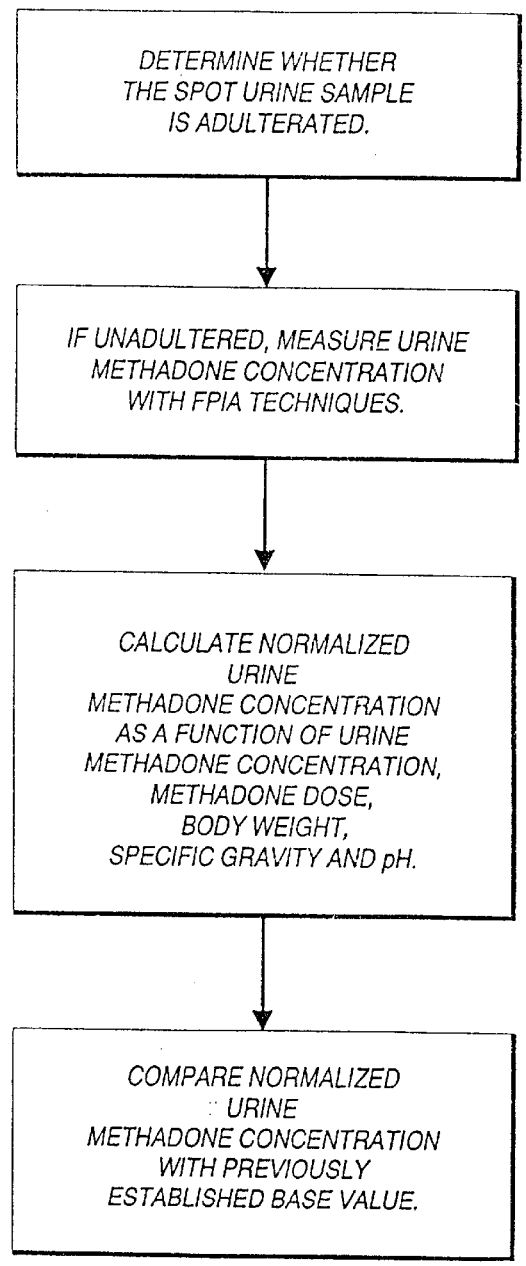

METHOD OF MONITORING PATIENT COMPLIANCE WITH MEDICATIONS PRESCRIPTIONS

REFERENCE TO RELATED APPLICATION

This is a continuation of application Ser. No. 08/248,102 filed on May 24, 1994 now U.S. Pat. No. 5,547,878 which is a continuation in part of Ser. No. 08/145,821 filed on Nov. 2, 1993.

TECHNICAL FIELD

The present invention relates to therapeutic drug ingestion monitoring. More particularly, the invention relates to methods of monitoring patients who are being prescribed potentially abusable or dangerous medications and have been placed on medication maintenance programs for compliance therewith.

BACKGROUND OF THE INVENTION

In the field of medicine and psychiatry, a number of medications, such as opioids, sedative-hypnotics, anticonvulsants, neuroleptics, and antidepressants, have been found safe and efficacious for the treatment of patients with biologically-based mental and physical illnesses. Patients placed on prescribed medication treatment plans are typically monitored. Subjective and objective methods are used to identify bothersome symptoms and to implement any changes necessary during the course of treatment. Monitoring generally continues for as long as treatment is provided. For example, the Hamilton Anxiety Scale can be used to quantify the amount of anxiety remaining as treatment proceeds. If the level of residual anxiety decreases significantly, say from the proper prescription of a benzodiazepine drug like diazepam, then the physician and patient can be assured that treatment is efficacious and should be continued.

Preferably both quantitative and analytical methods should be used to follow the patient on a repetitive basis to insure that the patient is indeed ingesting the prescribed amounts of medication in the proper manner and responding as expected. Currently, the most common method of monitoring patients for medication compliance is clinical observation which involves individual counseling and close personal supervision by physicians. Physicians observe physiological signs and symptoms such as intoxication, drug withdrawal typically occurring for benzodiazepines, barbiturates and opioids, or residual signs of illness such as tremor in anxiety, sighing in depression, and nociception in pain syndromes. Physicians also listen to patient complaints regarding degree of pain relief and evaluate psychological changes over time. This method however is time consuming, expensive and highly subjective. Needless to say, it is fraught with potential errors.

Additional compliance information can be obtained using qualitative urine monitoring methods such as the standard laboratory procedure called enzyme-multiplied immunoassay (EMIT). Utilizing an arbitrary cutoff value, these methods provide the clinician with a simple positive or negative indication of the possible presence or absence of a parent drug or its metabolites in a patient's urine. The parent drug is the prescribed medication itself and the metabolites are those chemical derivatives of the medication which naturally occur upon the patient's body metabolizing the medication. These tests do not provide information concerning the time or amount of last drug use or whether or not the prescribed dose of medication was ingested properly, diverted or supplemented.

Physicians utilizing only clinical evaluation and qualitative urine drug screening test results may develop problems in their treatment methods. Such is often the case in treating patients who have become biochemically dependent upon opioids either through prescription or illegal use. Opioid addicts experience great difficulty eliminating their dependency upon such drugs and typically enter into extended rehabilitative treatment programs which utilize prescribed methadone dosages to eliminate opioid dependency. Physicians must effectively assess the condition of patients on methadone maintenance programs in order to adjust dosages and monitor compliance. If a patient is continually testing positive for opioids or complains of continuing subjective opioid withdrawal symptoms, a physician may conclude that the currently prescribed dose of methadone is not sufficient to curb the body's desire for opioids and may increase the prescribed dosage. This highly subjective monitoring method can result in over-medication, patients being given more methadone than they require, creating an unnecessary reliance on methadone. Alternately, physicians sometimes conclude, erroneously, that a patient's methadone dose should be sufficient to prevent opioid withdrawal and drug cravings and deny the patient a further increase sufficient to stop illicit opioid use. Such action can expose the patient to further intravenous drug use and the associated negative social and medical consequences which can follow such as HIV, hepatitis, and blood poisoning.

Similar problems with treatment may arise for patients prescribed diazepam for longstanding generalized anxiety. Patients may not show improvement in their condition even though this therapy is known to be highly efficient. This medication is a member of the sedative-hypnotic family of benzodiazepines which have been clinically shown to cause sedation, hypnosis, decreased anxiety, muscle relaxation, anterograde amnesia and anticonvulsant activity. A patient, for example, may insist that he or she is ingesting the medication as prescribed, and yet claim no significant improvement in symptomology. The physician suspects that the patient is not ingesting the medication properly and perhaps is selling it, and orders a qualitative urine drug screen to verify compliance. The screen is reported as positive at greater than 200 ng/ml drug concentration. Since some benzodiazepine is present the physician assumes, incorrectly, that the patient is compliant, but will require additional medications and increases the daily dose. In truth, the patient is diverting the majority of his or her dose to the illicit market and only ingesting enough drug to test positive on the drug screen.

Patients also commonly visit multiple physicians to obtain similar medication for self-ingestion. These patients desire the intoxicating effects of the medication, but are unable to obtain sufficient quantities from a single source. Qualitative tests like the EMIT are generally not useful in detecting this situation since the quantitative amount of medication concentration in the body is not measured.

Another monitoring method sometimes used, though most often only in research centers, is direct measurement of parent drug concentrations or active metabolites concentrations of the drug in plasma. This method has been particularly useful to eliminate illicit opioid use of patients on methadone maintenance programs. It is known from analytical studies using venous blood samples obtained from stable patients that plasma methadone concentrations ranging from 150–600 ng/ml are necessary. This direct method is not very practical since it requires the use of time consuming, expensive, and highly technical analytical procedures such as high pressure liquid chromatography and gas chromatography/ mass spectrometry since active and inactive metabolites must be quantified separately. Additionally, for many patients the obtaining of plasma samples is invasive, offensive and difficult due to inadequate venous access. Medical professionals must also be concerned about their own health safety in doing this since they are exposed to blood products from patient groups which can have a high prevalence of hepatitis and HIV infection. Therefore, such procedures are primarily conducted in research centers and not generally utilized in standard maintenance programs.

While providing useful information relative to patient status and treatment compliance, the clinical monitoring methods described above, i.e. clinical interviews with patients, direct plasma drug measurement and qualitative urine drug screening, have distinct drawbacks which limit their usefulness in extended treatment programs. Therefore, it is seen that a need remains for a better method of monitoring patients who have been placed on potentially abusable and dangerous maintenance medications for compliance therewith. To help prevent continued medication misuse and better optimize patient medication dose, it would be advantageous for patients to have a facile bodily fluid, such as urine, regularly and quantitatively monitored for the presence of the medication. Such a monitoring method would help physicians both in prescribing adequate doses of medication and in monitoring patients to insure that they were only ingesting the prescribed amounts. Obtaining a fluid sample like urine would not be invasive to the patient or a safety risk to the health care provider. Accordingly, it is to the provision of such improved methods that the present invention is primarily directed.

SUMMARY OF THE INVENTION

In co-pending application Ser. No. 08/145,821 it is disclosed that patients in methadone maintenance programs can be monitored for compliance by sampling and analyzing a patient's urine for methadone concentration as an indicator of plasma methadone concentration which in turn provides a correlation to methadone dose ingested. This information is used to monitor the patient's compliance with a prescribed methadone program and to establish the proper methadone dose. First, it is preferable to determine whether the urine sample is indeed from the patient in question and whether the urine sample is adulterated as by comparing urine pH, specific gravity, and creatinine level with that of normal urine and specific values previously determined for the patient. If found to be unadulterated and probably from the patient in question, the raw urine medication concentration is measured with standard quantitative laboratory methods. For example, the urine sample may be measured using high pressure liquid chromatography or gas chromatography/ mass spectrophotometry, but preferably by using fluorescence polarization immunoassay (FPIA) because of its ease and rapidity of analysis. FPIA is employed such as with an Abbott TDX or ADX Analyzer.

Once an analytical value has been determined for the actual concentration of methadone in the sample, adjustments are made to account for the effects of variations in certain urinary parameters upon this concentration. A relationship exists between the actual concentration of methadone adjusted for compounding effects of urine specific gravity, the renal clearance of methadone as a function of urine pH, and the concurrent plasma methadone concentration. By obtaining multiple urine samples from a patient, once or twice a week, it is possible to establish a stable, baseline, 24-hour trough plasma methadone concentration for each patient against which a current or future value can be statistically compared.

It was also disclosed that the actual urine methadone concentration can be converted to a urinary parameter-normalized urine methadone concentration. The calculation incorporates the measured actual urine methadone concentration, urine specific gravity, and the pharmacokinetic parameters associated with metabolizing methadone of methadone dose, patient's body weight, and urine pH. By establishing an individual's expected value for the urinary-parameter normalized urine methadone concentration, subsequent readings may be compared with the expected value to evaluate whether the patient is compliant with his or her prescribed dose.

It has now also been discovered that a patient's urine may also be analyzed for parent drug and its metabolites concentrations as a method of monitoring compliance with a prescribed medication dosage. (Hereinafter the term "medication concentration" and "parent drug concentration" shall also be understood to include their metabolites.) A normalized urine medication concentration (nu) is determined by a relationship discovered to exist between urine specific gravity and raw urine parent drug and its metabolites concentrations. A urinary-parameter normalized urine medication concentration ($nu_p$) may also be determined by the pharmacokinetic manipulation of the normalized urine medication concentration. Both nu and nu, are utilized once or repetitively for determining patient compliance with prescribed medication dosage.

The normalized urine medication concentration is a constant value for each patient and may be compared to an individual's expected nu once such is established or to a group of nu. The individual's expected nu is established by obtaining multiple urine samples from a patient once or twice a week and evaluating those samples for nu to obtain historical data on that patient. If the current nu is compared to and found to be similar to the expected nu, then the patient is deemed in compliance. This method of monitoring compliance is dependant upon the assumption that a patient is initially compliant in order to obtain the expected value.

In determining normalized urine medication concentration the urine is preferably first tested for adulteration in the same manner as discussed above. If found to be unadulterated, the urine methadone concentration is measured with standard quantitative laboratory methods, preferably FPIA. Once an analytical value has been determined for the raw concentration of medication in the urine sample, a normalized urine medication concentration is calculated in accordance with its relationship to specific gravity as hereinafter described.

Alternatively, for clinical situations the urinary-parameter normalized urine medication concentration is preferably utilized since an individual's expected value need not be established. Instead, the urinary-parameter normalized urine medication concentration is compared with an expected $nu_p$ value of an average patient for the maintenance program prescribed. This method is particularly applicable for potentially abusable or dangerous medications such as antidepressants, anticonvulsants, beta-blockers, alpha agonists and antagonists, neuroleptics, analgesics, antirheumatics, and chemotherapy agents.

The $nu_p$ is calculated by adjusting the normalized urine medication concentration for compounding effects of urine pH, medication dose, patient body weight, urine flow rate and other pharmacokinetic parameters associated with the metabolism of a particular drug. The expected $nu_p$ value of an average patient was established by obtaining numerous samples of controlled compliant patients on prescribed doses of medication and evaluating those samples for $nu_p$. If the current value of the $nu_p$ is within ±20 percent of the $nu_p$ value expected of the average patient on the same prescribed dose, the patient is considered to be in compliance with his or her prescribed dose.

Compliance may also be confirmed by using the current urinary-parameter normalized urine medication concentration to estimate the correlating daily medication dose from a previously developed empirical graph of urinary-parameter normalized urine medication concentration (ng/ml) versus daily oral medication dose ingestion (mg/day) for the general population. If the estimated daily medication dose is not the prescribed medication dose, then the patient is not in compliance.

BRIEF DESCRIPTION OF THE DRAWINGS

FIG. 1 is a block diagram of a preferred method of the invention as it relates to a methadone maintenance program.

FIG. 2 is a block diagram of another preferred method of the invention as it relates to a methadone maintenance program.

METHADONE MAINTENANCE PROGRAMS

Figure 6:
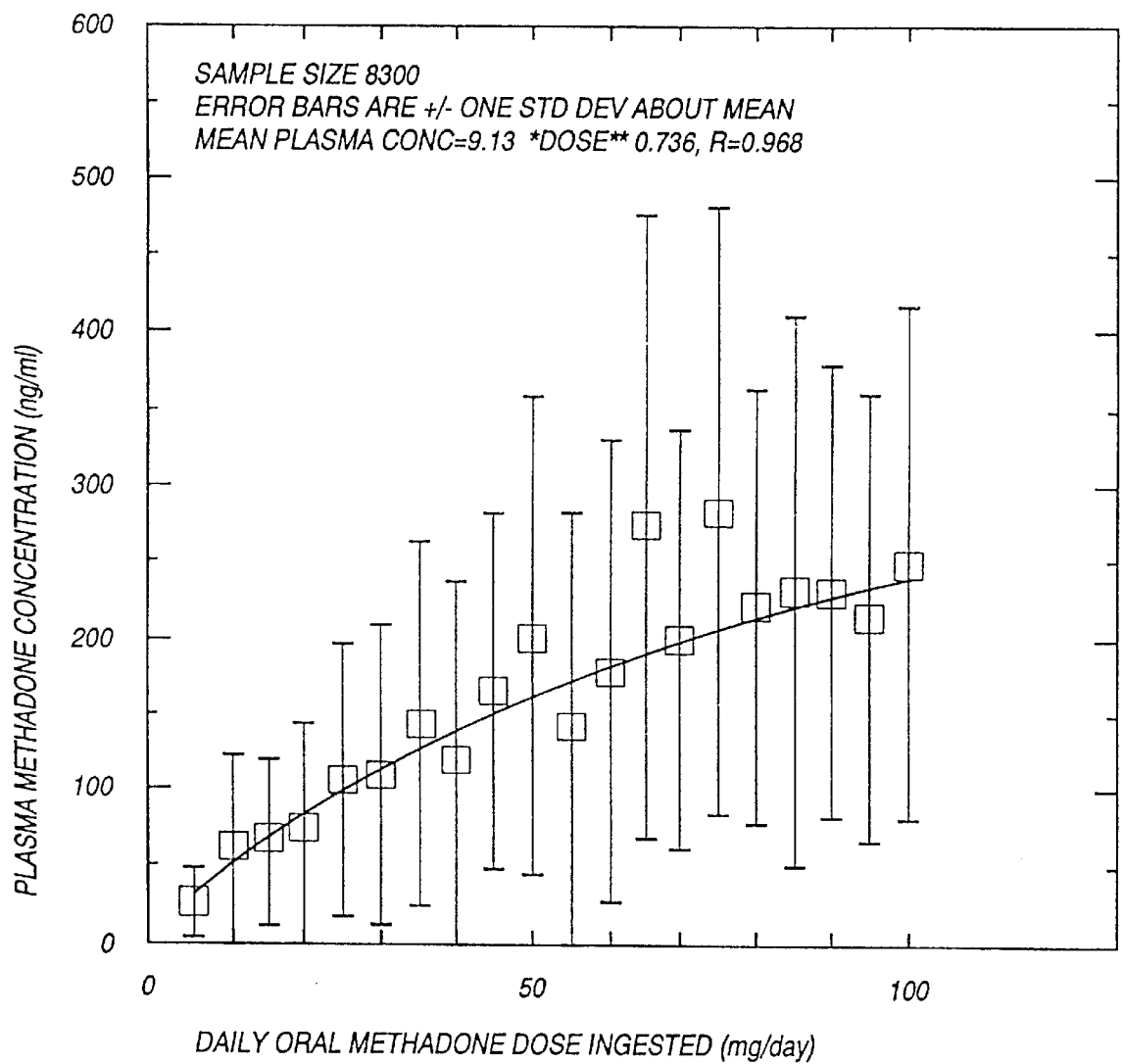
FIG. 6 is a graph of plasma methadone concentration versus daily oral methadone dose.

For methadone maintenance programs, the optimum 24-hour trough plasma methadone concentrations is between 150–600 ng/ml, which has been generally recognized in past studies as most effective in deterring illicit opioid use. A patient's 24-hour trough plasma methadone concentration, as calculated by the present method, is compared to a previously developed empirical graph of plasma methadone concentration (ng/ml) versus daily oral methadone dose ingestion (mg/day) for the general population. The graph, as shown in FIG. 6, represents the 24-hour trough plasma methadone concentration expected for the average patient comprising the cohort from which the general population data was generated. The comparision helps a physician determine both how the patient is metabolizing methadone, what the most likely final methadone dose will be to attain the 150–600 ng/ml level, or whether the patient is compliant with his or her prescription.

Over time, a unique plasma concentration-daily methadone dose relationship is derived for each individual patient which can be compared to the relationship expected for that particular patient or for an average patient. If the two relationships are not similar, the patient's metabolism rate may account for any over- or under-effectiveness of the prescribed dose. A physician, in accounting for the patient's individual metabolism rate, can now optimize the patient's methadone dose to achieve an efficacious and safe plasma methadone concentration. Further, once the optimum methadone dose is established for the patient, the physician can monitor the patient for compliance with his or her prescribed dose by comparing the plasma methadone concentration of methadone, as calculated by the present method, with his expected, historical plasma methadone concentration for that particular methadone dose to reveal any covert methadone diversion or supplementing.

Testing for Adulteration

First, a supervised, spot sample of urine is collected from a patient. Several properties of the urine are measured to evaluate whether the urine is adulterated, adulteration being the altering by a patient of his or her urine in an effort to prevent detection of illicit drug use or diversion of methadone. Adulteration typically is accomplished by adding foreign substances to the urine such as salt, bleach, or vinegar. Many patients attempt to dilute amount of drugs in the urine sample by drinking large quantities of water or by adding water to the sample. Adulteration may also occur by substituting another person's urine for the patient's own urine, including instillation of foreign urine into the patient's bladder.

In checking for adulteration, urine pH is measured, as with the use of a pH Data Logger type meter available from Oakton, to see if it is within the normally expected pH range of 4.5 to 8.5. Urine specific gravity is also measured to see if it is within the normal range of 1.004 to 1.035 units. A Digital Urinometer by Biovation may be used for this test. Creatinine, an end product of glycine and arginine metabolism excreted through the kidneys, is measured to evaluate renal function. The creatinine level in human urine usually ranges from 8 to 500 mg/dl, the range being affected by variables such as age, sex, diet, lifestyle and geographic location. Creatinine levels generally are homeostatically maintained by the body at a constant value for each individual patient over his or her lifetime. Creatinine levels may be determined on many different analyzers, including a TDx REA Creatinine System available from Abbott Laboratories. All of these tests are helpful in establishing normally expected ranges for each patient and the overall population of patients.

Once pH, specific gravity, and creatinine level values for the spot urine sample are obtained for a particular patient, comparisons can be made between the sample in question and values previously measured (if already available) both for the patient and for normals to ascertain whether the urine sample is adulterated. If no adulteration is found, a data base is created or extended for the patient so that a basis of comparison exists for future spot urine samples. Of the three measures, urinary creatinine level is generally the most useful indicator as to whether the spot sample is that of the patient or of someone else.

Determination of Raw Urine Methadone Concentration

The unadulterated sample is next analyzed for raw urine methadone concentration, preferably using fluorescence polarization immunoassay (FPIA) technology. In this regard an Abbott TDX or ADX Analyzer may be profitably employed. Other standard analytical methods may also be used such as chromatography or other types of immunoassay. The value obtained is the raw urine methadone concentration, u.

Determination of Plasma Methadone Concentration

Plasma methadone concentration is obtained from the raw urine methadone concentration by utilizing a standard dimensionally correct relationship known as the renal clearance, which is, $$cl=(u \cdot v)/p \qquad (1)$$

where cl is renal clearance (ml/min), u is raw urine methadone concentration (ng/ml), v is the volume of urine collected in time (ml/min) or otherwise known as the urine volume production rate, and p is the measured plasma methadone concentration at the midpoint of the collection period (ng/ml).

Figure 3:
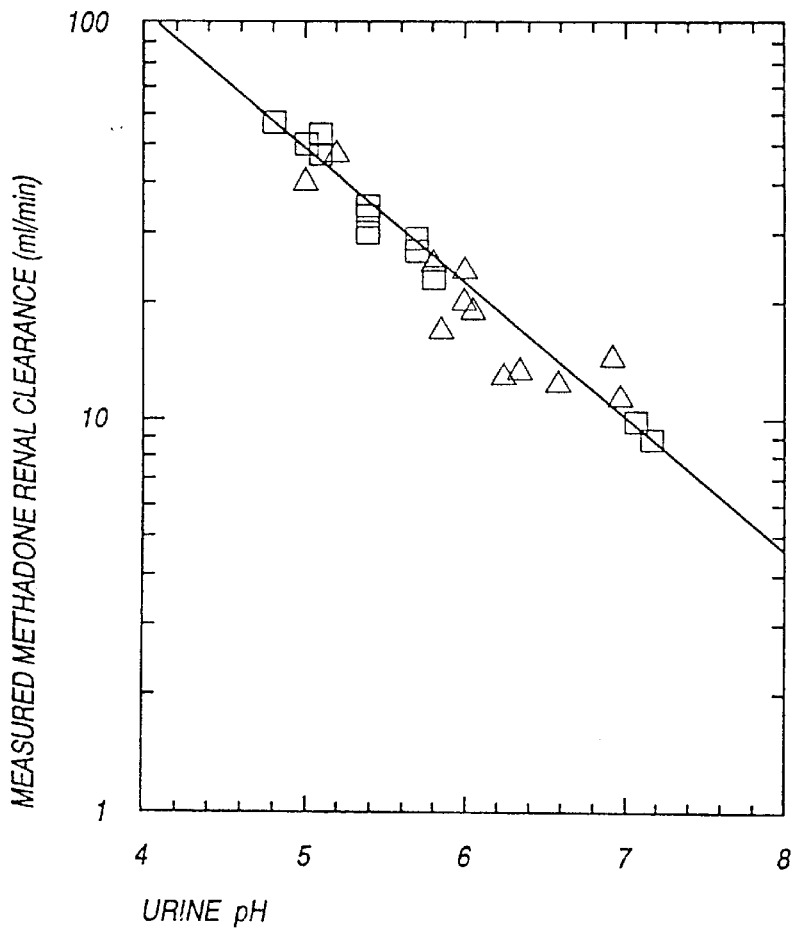
FIG. 3 is a graph of measured methadone renal clearance versus urine pH.

Since the actual, current renal methadone clearance is not generally known for any one patient, nor can it easily be directly measured under normal clinic conditions, it must be estimated from an empirical relationship. From experiments measuring urine and plasma methadone concentrations over timed collection periods (which recognizes that the renal clearance for methadone is strongly affected by urinary pH because of the weakly basic properties of methadone), it has now been found that renal clearance relates to urine pH in the range 4.8–8.7 (see FIG. 3) as, $$cl=104,218 \cdot pH^{(-4.76)} \qquad (2)$$

and for which generally, a strong dependence upon actual patient weight is not noticed.

Rearranging Equation (2), the plasma concentration of urine may be calculated as follows, $$p=u \cdot v/cl \qquad (3)$$

The actual, raw urine methadone concentration is known from the FPIA results. Renal clearance can be calculated from Equation (2) by utilizing the urine pH previously measured in testing for adulteration. However, actual values of the urine volume production rate, v, are not available since routine clinical urine sampling procedures only provide a point-in-time or spot urine sample.

Heretofore, it has been thought to be impossible to calculate plasma methadone concentration of a drug from the spot urine sample and that a timed urine collection must be done (usually 24 hours). It has now been found that these beliefs are flawed.

It is now appreciated that renal excretion rates (mg/min) for drugs and urine metabolites are relatively constant for any patient during a typical day. This constancy has now been experimentally verified by examining the renal excretion rates of methadone, benzodiazepines, other drugs and creatinine and other endogenous metabolites as a function of urine volume production rate. For example, sequential, complete and timed (1–8 hours holding periods) aliquots of urine for 12 compliant control subjects were collected over 24 to 72 hour periods. For each and every urine aliquot, urine volume production rate (ml/min), specific gravity and creatinine concentration (ng/ml) were determined.

Using this data, a dimensionless, linear relationship was found to exist that is the same for all patients, between a urine volume production rate factor (UVPRF) and a reverse urine creatinine excretion factor (RUCEF). For each individual, control, urine collection period, the UVPRF is defined by the ratio of urine volume production rate for each urine aliquot collected, v, to the urine volume production rate for the most concentrated sample in the collection period with a specific gravity usually near 1.030, v', $$UVPRF=v/v'. \qquad (4)$$

The RUCEF factor is defined by the ratio of the creatinine concentration of the most concentrated urine aliquot with a specific gravity usually near 1.030, u', to the creatinine concentration for each urine aliquot collected, u, $$RUCEF=u'/u. \qquad (5)$$

Figure 4:
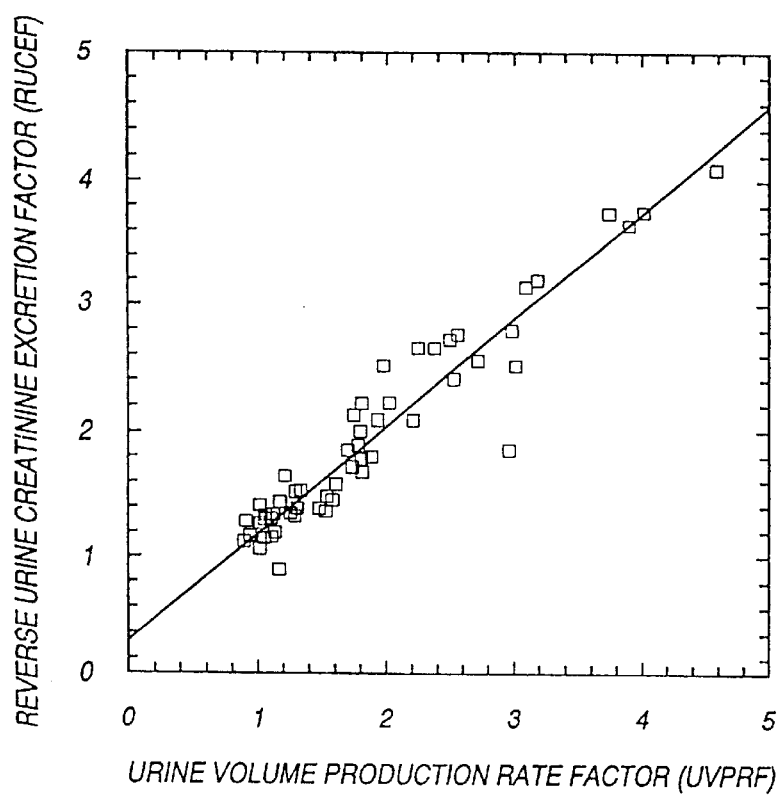
FIG. 4 is a graph of reverse urine creatinine excretion factor (RUCEF) versus urine volume production rate factor (UVPRF).

This linear relationship is shown in FIG. 4. The best fit linear regression line is given by the expression, $$RUCEF=0.942(SE\ 0.013) \cdot UVPRF+0.121(SE\ 0.043) \qquad (6)$$

$$u'/u=0.942 \cdot v/v'+0.121 \qquad (7)$$

adjusted squared multiple R=0.985, standard error (SE) of estimate=0.242, F-ratio 4965.

Therefore, contrary to the traditional teachings of those skilled in the art, urine drug and metabolite concentrations, u, are inversely related to the volume of urine produced by the kidneys, v, clearly demonstrating that the product (u·v) is constant at any particular time point and urine pH (given a steady-state plasma methadone concentration p and renal clearance cl).

Since p, cl, and (u·v) at any time point and urine pH are constant, steady-state values,. it follows that from Equation (7) some empirical mathematical relationship must exist between u and v such that given an arbitrary urine volume production rate v' and an equivalent u' at a reference point (specific gravity 1.030):

$$\{u \cdot v\}_{sg\ actual}=\{u' \cdot v'\}_{sg\ 1.030} \qquad (8)$$

or upon rearrangement for u' gives, $$u'=u \cdot (v/v') \qquad (9)$$

where the products given in Equation (9) are those measured for a spot urine collected with an actual specific gravity and a corrected specific gravity typical of a morning void of 1.030.

Figure 5:
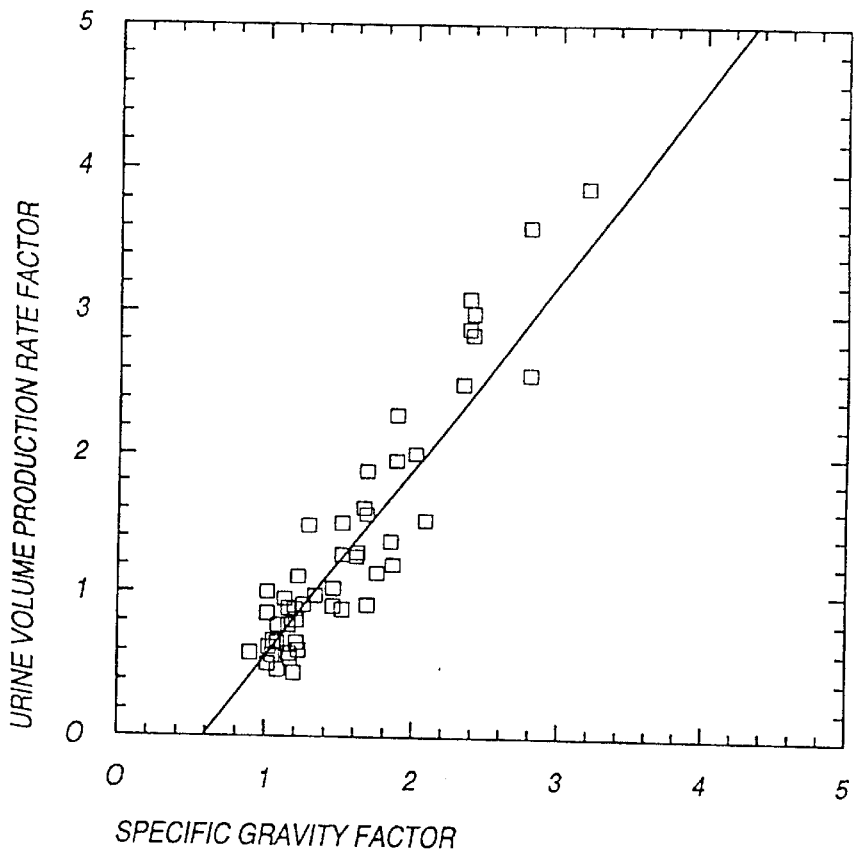
FIG. 5 is a graph of urine volume production rate factor (UVPRF) versus specific gravity factor (SGF).

Using controlled urine collections, a urine volume production rate v' of 0.44 ml/min for persons with reasonably normal renal functions at a specific gravity of 1.030 was measured. It has also been discovered that a linear relationship exists-between the urine volume production rate factor and the specific gravity factor (SGF), {(1.030−1.000)/(sg−1.000)}, as shown in FIG. 5 and given as follows:

$$UVPRF=v/v'=2.43(SE\ 0.106) \cdot SGF-1.43(SE\ 0.216) \qquad (10)$$

where the adjusted squared multiple R=0.856, standard error of the estimate=0.787, F-ratio 482.

Combining all of the above considerations, plasma methadone concentrations can be calculated by substituting Equations (2, 8, 9 and 10) in Equation (3):

$$p = u \cdot v/cl = u' \cdot v'/cl \qquad (11)$$
$$= v' \cdot u \cdot (v/v')/cl$$
$$= 0.44 \cdot u \cdot (2.43 \cdot SGF - 1.43)/104,218 \cdot pH^{(-4.76)}$$

where values of u, specific gravity, and pH are known from previous test results on a patient's spot urine sample. The equation may be more generally expressed as follows:

$$p = k_3 \cdot u \cdot (k_1 SGF - k_2)/k_4 \cdot pH_{(-k5)} \qquad (11a)$$

wherein $k_3$ is a constant approximately equal to 0.44, $k_1$ is a constant equal to 2.43, $k_2$ is a constant equal to 1.43, $k_4$ is a constant equal to 104,218 and $k_5$ is a constant equal to 4.76.

Comparing Patient's Calculated Plasma Methadone Concentration to that of an Average Patient for the Same Dose Once the plasma methadone concentration is calculated from Equation (11), it is compared with the plasma methadone concentration expected from an average patient on a similar daily methadone dose as shown in FIG. 6, which demonstrates how plasma methadone concentration varies with dose for the standard population. FIG. 6 was developed by utilizing data from 8300 urine samples from 150 methadone maintenance patients on controlled daily methadone dosages.

Using this figure, a clinician can estimate how a prescribed dose will effect a patient's methadone plasma level. For example, a patient on a 70 mg/day methadone dose is expected from FIG. 6 to have a plasma methadone concentration of 200 ng/ml. However, from the spot urine sample the calculated plasma methadone concentration is 100 ng/ml thereby indicating that the patient's body is quickly metabolizing the methadone and a higher dose is needed or that the patient is diverting the methadone to others or that the patient is simply not using it. Higher concentrations per dose suggest the opposite of the above. Knowing that the plasma methadone concentration does not correlate to the prescribed methadone dosage, the clinician now has valuable information to evaluate the next step in the patient's program.

An optional use of the calculated plasma methadone concentration is for estimates of the methadone doses that a patient has taken. FIG. 6 is used to estimate the patient's methadone dose by adjusting the calculated plasma methadone concentration relative to any parameters of the patient that fall outside the average patient parameters, such as patient body weight, methadone plasma half-life, and time of ingesting dose.

Verification of Plasma Methadone Concentration Equation (11)

In order to ascertain the effectiveness of the plasma methadone concentration formulation, blood and urine samples were taken from a control group of patients. Urine and blood samples were simultaneously analyzed for plasma methadone concentration using FPIA and GC/MS. The urine methadone concentration was converted to a calculated plasma methadone concentration utilizing the formulation of the present invention in Equation (11).

Figure 7:
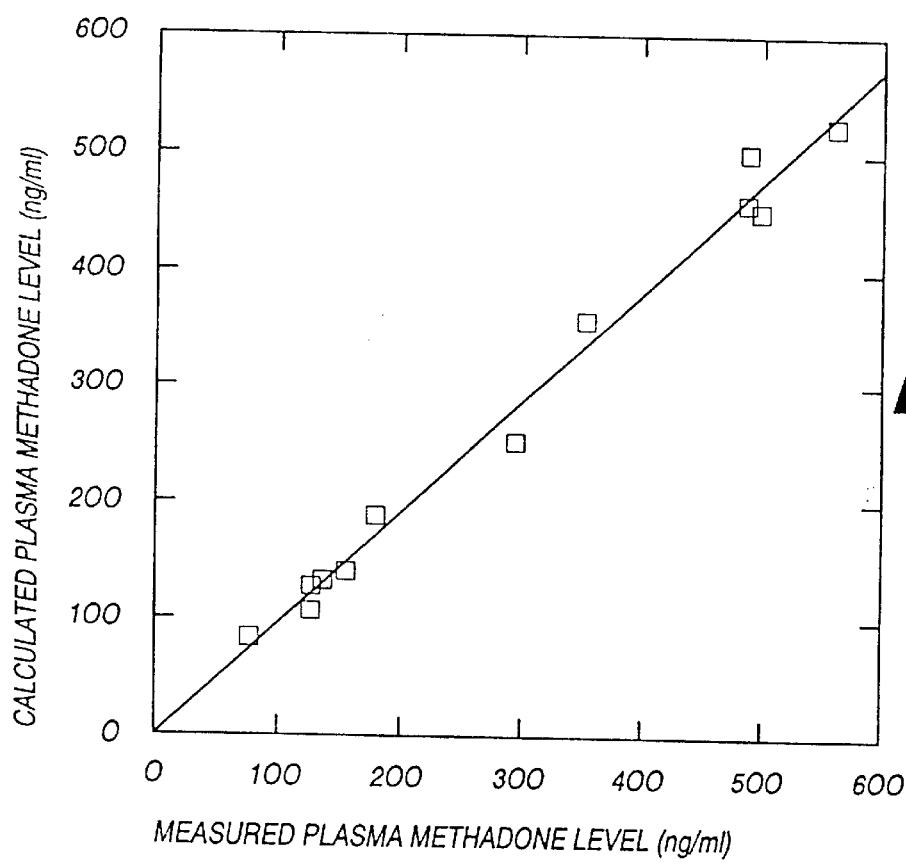
FIG. 7 is a graph of plasma methadone concentration calculated using the method of the present invention versus measured plasma methadone concentration using Abbott fluorescence polarization immunoassay (FPIA).

Referring now to FIG. 7, the accuracy of calculating plasma methadone concentration from urine methadone concentration is verified by the excellent linear agreement between the plasma concentrations calculated by the present method from random, spot urine measurements and concurrently measured plasma methadone concentrations using actual blood samples: Estimated=0.970 (SE 0.034) ·Measured–1.25 (SE 11.495), adjusted squared multiple R=0.987, standard error of estimate=20.155, F-ratio 810.

Determination of Urinary-Parameter Normalized Urine Methadone Concentration

The parameters of a patient's urine, such as pH and specific gravity, vary from one day to the next dependant upon the type and quantities of foods and beverages ingested. Additionally, individuals metabolizes these substances, as well as methadone, at different rates. To account for these variations, a urinary-parameter normalized urine methadone concentration, $nu_p$, is calculated that adjusts measured raw urine methadone concentration, u, in accordance with a prescribed methadone dose, urine specific gravity, patient's current body weight (lbs) and urine pH. The relationship between u, pH, dose and specific gravity was empirically developed using nonlinear regression analysis. Results were normalized to a dose level of 80 mg/day, a patient weight of 154 pounds, and urine pH of 6.5 giving the final equation for monitoring a patient's $nu_p$ in Equation (12) as follows:

$$nu_p = (80/DOSE)^{0.823} \cdot (6.5/pH)^{-4.838} \cdot (BODY\ WEIGHT/154) \cdot UVPRF \cdot u$$

The equation may be generally expressed in Equation (12a) as follows:

$$nu_p = (k_3/DOSE)^{k_4} \cdot (k_5/pH)^{k_6} \cdot (BODY\ WEIGHT/k_7) \cdot u \cdot (k_1 \cdot SGF - k_2)$$

wherein $k_3$ is a constant equal to 80, $k_4$ is a constant equal to 0.823, $k_5$ is a constant equal to 6.5, $k_6$ is a constant equal to 4.838, $k_7$ is a constant equal to 154, $k_1$ is a constant equal to 2.43 and $k_2$ is a constant equal to 1.43.

The urinary-parameter normalized urine methadone concentration is statistically constant and unique for each patient regardless of an individual's methadone metabolism and daily changes in urine parameters. Thus, a patient's expected $nu_p$, once established accurately for an individual patient within a statistical margin of error, may be used to evaluate methadone diversion or supplementation in patients by comparing subsequent calculations of $nu_p$ with the patient's particular expected value of $nu_p$. If the subsequent calculation is similar to the expected value, the patient is complying with his prescribed dose.

The generation of a patient's $nu_p$ expected value is done using standard statistical techniques developed for relating the mean and standard deviation observed from a particular sampling distribution (of size n elements) to the mean and standard deviation expected for the whole population of values, both for each patient and the population of all patients. For further details one can refer to the text, *Hahn G J, Meeker W Q, Statistical Intervals, John Wiley and Sons,* 1991.

To utilize such techniques it is first necessary to determine what the expected standard deviation is for the whole population of compliant patients under observation. Previously, it had been observed that although mean values for $nu_p$ are different for each patient, the observed variability about the mean for compliant patients is quite consistent and similar to the overall cohort of compliant patients; suggesting that the following statistical technique can be utilized.

Sequential, urine data was retrieved from computer files for 216 patients (13,000 data points) and transferred into a commercial statistical/graphical package produced by Systat, Inc. Each patient's data was sorted individually by ascending concentration for initial data review. All data points having unusual creatinine values <10 or >500 mg/dl or a methadone concentration <300 or >60,000 ng/ml were discarded as being suspect and non-physiologic. Additional outliers were eliminated from each patient file using manual review (preliminary statistic data were available as a guide). For statistical reasons, all patients having less than 10 acceptable data points were also eliminated.

Using the remaining data sets for each patient (180 persons, approximately 12,000 individual urine values), individual $nu_p$ values were obtained from which individual means and standard deviations were calculated.

Utilizing this data, a plot of sample size (for each patient) versus calculated sample standard deviation (for each patient) was generated. Approximately, 180 individual, standard deviations (y-axis) were plotted against samples sizes ranging from 10 to 200 (x-axis). Using standard 95% confidence limit tables from *Hahn and Meeker*, lower and upper limits were co-plotted on the above curve by adjusting the overall population standard deviation until the data bounded by the prediction curves enclosed all acceptable data. The average population standard deviation for the set of acceptably, compliant patients was found to be about 3000 for this particular set of patients, though it could be lower if further restrictions to the initial data set were applied. In general, the average population standard deviation varies linearly with mean $nu_p$, and considering this effect the acceptable range for a particular patient can be narrowed.

Given this value, another set of prediction equations specifying the allowable range for the next measured nup for a particular patient, given a sample size of n, a mean $nu_p$ for an individual patient and either the patient standard deviation or the population standard deviation (whichever is least), can be calculated as shown in *Hahn and Meeker*. If the measured value is within the acceptable statistical range, given a previously calculated mean and standard deviation, then it is accepted. If the value is too high or too low, this is marked on the urine drug screen under the column called Pred, as shown in clinical cases #'s 4 and 5, Tables F and G.

An alternative method which can be used to establish outliers for each patient data set, which is also statistically sound, is based upon the ratio of the currently determined $nu_p$ to the mean $nu_p$ calculated from previous values for an individual (usually a minimum of 3 to a maximum of 12, though any larger number of samples could be used.) By plotting log normal histograms of these calculated ratios for the same patient data set mentioned above, the expected variation about the most common value of unity for the entire population is determined. Ninety-nine percent confidence limits are distributed in a skewed manner about the value unity and range between about 0.43 to 2.30. Therefore, given a current mean $nu_p$ for a particular patient, the acceptable values can be found by simple multiplication using 0.43 times $nu_p$ for the lower limit and 2.30 times $nu_p$ for the upper limits. Other confidence intervals are easily determined as well.

Verification of Urinary-Parameter Normalized Urine Methadone Concentration Equation (12)

Shown in Table A is a partial representation of data from a standard computer printout for a compliant patient in which is summarized both urine parameters and methadone concentrations. The last column in the figure represents the urinary-parameter normalized urine methadone concentration values for the patient which are quite constant once sg, pH, dose corrections are made to the raw urine methadone concentration. CR represents the specific gravity corrected urine creatinine concentration which should have a CV of less than 15 percent.

TABLE A

| Date | Dose | Temp | pH | SG | CR | u | p | $nu_p$ |
|---|---|---|---|---|---|---|---|---|
| 04-20-92M | 70 | 98.0 | 5.40 | 1.022 | 335 | 6838 | 167 | 6966 |
| 04-15-92W | 70 | 96.0 | 5.70 | 1.024 | 268 | 6536 | 176 | 7381 |
| 04-13-92M | 70 | 96.0 | 5.90 | 1.019 | 271 | 5462 | 259 | 10913 |
| 04-10-92F | 70 | 98.0 | 5.70 | 1.021 | 377H | 5180 | 177 | 7430 |
| 04-06-92M | 70 | 98.0 | 5.90 | 1.028 | 261 | 7398 | 171 | 7208 |
| 04-02-92h | 70 | 96.0 | 5.70 | 1.026 | 271 | 5990 | 149 | 6254 |
| 03-30-92M | 70 | 94.0 | 5.60 | 1.021 | 303 | 4203 | 132 | 5532 |
| 03-25-92W | 70 | 98.0 | 5.20 | 1.021 | 271 | 8469 | 187 | 7790 |
| 03-24-92T | 70 | 98.0 | 6.00 | 1.023 | 243 | 3736 | 139 | 5852 |
| 03-20-92F | 70 | 96.0 | 5.80 | 1.024 | 272 | 5601 | 164 | 6881 |
| 03-16-92M | 60 | 94.0 | 5.30 | 1.022 | 286 | 7049 | 157 | 7448 |
| 03-13-92F | 60 | 96.0 | 5.70 | 1.019 | 277 | 4935 | 199 | 9473 |
| | | | | Mean: | 287 | 5950 | 173 | 7427 |
| | | | | SD: | 35 | 1372 | 33 | 1492 |
| | | | | CV: | 12.2 | 23 | 19.1 | 20 |
| | | | | Tests: | 12 | 12 | 12 | 12 |

Clinical Examples

Case #1

J. S. is a 52 year old woman with right-sided, migraine headaches with aura beginning after her hysterectomy at age 44 and prior to regular use of any medication. Her migraines began with flashes of light and blurry vision in either eye. Often "a film covers my right eye." Prodromata was usually followed by right retro-orbital pain accompanied by photophobia and nausea. This patient also suffered tension headaches and headaches secondary to allergic rhinitis. She was able to clinically differentiate migraine and tension components of her headaches, as the migraine component was refractory to multiple trials of ergot alkaloids, benzodiazepines, NSAIDs, beta-blockers, calcium channel blockers and psychotherapy. Multiple CT scans had been normal.

J. S. had been biochemically dependent upon prescription opioids to relieve migraine pain for over a year prior to her referral to a methadone maintenance clinic. According to Federal Register 21 CFR Part 291, a person biochemically dependent (this is the current definition for opioid dependency utilized by the federal government) to narcotics for more than a year qualifies to enter into a methadone maintenance program.

J. S.'s situation was similar to that of approximately 0.5% of the general, adult population of the United States who are also biochemically dependent upon opioid medications because of legitimate medical illness and disease. Oftentimes, it is difficult for the clinician to determine whether or not the patient is currently using opioids for relief from organic pain or is treating the psychological sequelae of their disability. In either case, methadone maintenance was the most efficacious choice to help and protect the patient.

J. S. enrolled in the methadone maintenance program 36 months ago for pain management. Gradual titration to 45 mg of methadone was achieved over a short time period during which migraines slowly decayed in frequency and severity. During her time in treatment she had subsequently suffered only 2 migraine attacks which were greatly reduced in intensity. Both attacks were related to a transient decrease in plasma methadone levels below 80 ng/ml secondary to vomiting associated with viral syndromes.

A urine history is shown in Table B for this patient showing both estimated plasma methadone levels and the urinary parameter-normalized methadone concentration.

vision, subsequent unilateral headaches were invariably accompanied by nausea and vomiting, photophobia, and hypersensitivity to motion of her head and to cigarette smoke. Despite trials of biofeedback, physical therapy, and medications (trials of beta blockers, calcium channel blockers, ergot alkaloids over the years) and drug holidays; the frequency of her headaches had increased over the years to nearly daily occurrence. Lumbar punctures and multiple CT and MRI scans of her head were normal.

Following failure of self-administered IM administration of nalbuphine to control her pain, she began methadone maintenance 24 months ago. Because of many years of prior use of barbiturate-containing compounds her hepatic metabolic function was significantly enhanced requiring more than normal amounts of methadone—as shown by urine plasma concentration estimates. After stabilization on 130 mg per day of methadone, her migraines ceased completely at a plasma methadone level above 135 ng/ml. She continued to experience infrequent stress-related headaches, which were slowly decreasing in severity and frequency.

Urine histories are shown for this patient in Tables C and D. Notice how plasma methadone levels had increased in this patient over time as hepatic function returned to normal by discontinuing barbiturate-containing compounds (bar).

TABLE B

| Date | Dose | Temp | pH | SG | CR | u | p | $nu_p$ |
|---|---|---|---|---|---|---|---|---|
| 07-01-93h | 45 | 94.0 | 7.70 | 1.012 | 319 | 1069 | 348 | 21153 |
| 06-21-93M | 45 | 94.0 | 6.90 | 1.008 | 265 | 1336 | 401 | 25720 |
| 06-14-93M | 45 | 94.0 | 6.60 | 1.011 | 273 | 2109 | 368 | 22145 |
| 06-07-93M | 45 | 95.0 | 7.30 | 1.011 | 270 | 1883 | 399 | 32208 |
| 06-03-93h | 45 | 98.0 | 7.00 | 1.010 | 254 | 646 | 168 | 10174 |
| 05-27-93h | 456 | 94.0 | 7.60 | 1.018 | 269 | 1246 | 215 | 13051 |
| 05-20-93h | 45 | 95.0 | 6.80 | 1.011 | 275 | 1285 | 259 | 15585 |
| 05-13-93h | 45 | 95.0 | 7.80 | 1.011 | 272 | 757 | 293 | 17845 |
| 05-03-93M | 45 | 97.0 | 5.50 | 1.020 | 357H | 4094 | 153 | 7585 |
| 04-29-93h | 45 | 94.0 | 6.70 | 1.014 | N/T | 1318 | 180 | 10815 |
| 04-22-93h | 45 | 96.0 | 6.80 | 1.020 | 320 | 3900 | 335 | 20168 |
| 04-12-93M | 45 | 94.0 | 7.20 | 1.009 | 260 | 915 | 310 | 18777 |
| | | | Mean: | | 285 | 1713 | 285 | 17265 |
| | | | SD: | | 32 | 1146 | 90 | 5439 |
| | | | CV: | | 11.3 | 66.8 | 31.2 | 31.5 |
| | | | Tests: | | 11 | 12 | 12 | 12 |

Case #2

A. N. is a 44 year old woman whose migraine with aura began approximately 20 years ago. Beginning with blurred

TABLE C

| Date | Dose | Temp | pH | SG | CR | bar | u | p | $nu_p$ |
|---|---|---|---|---|---|---|---|---|---|
| 06-01-91S | 100 | N/T | 5.10 | 1.021 | 200 | HI | 6338 | 127 | 3243 |
| 05-29-91W | 100 | N/T | 5.40 | 1.021 | 184 | 2370 | 1985 | 52 | 1339 |
| 05-25-91S | 100 | N/T | 5.40 | 1.020 | N/T | N/T | 1360 | 39 | 995 |
| 05-22-91W | 100 | N/T | 5.10 | 1.013 | N/T | N/T | 1511 | 62 | 1582 |
| 05-20-91M | 100 | N/T | 5.10 | 1.005 | 134 | HI | 615 | 80 | 2026 |
| 05-18-91S | 100 | N/T | 5.40 | 1.017 | N/T | N/T | 2067 | 76 | 1952 |
| 05-15-91W | 80 | N/T | 5.40 | 1.019 | 129 | HI | 1120 | 35 | 1070 |
| Os-13-91M | 65 | N/T | 5.70 | 1.009 | 72 | HI | 335 | 37 | 1367 |
| 05-11-91S | 65 | N/T | 5.10 | 1.016 | 182 | HI | 816 | 25 | 911 |
| 05-08-91W | 50 | N/T | 5.40 | 1.010 | N/T | N/T | 853 | 65 | 2924 |

TABLE C-continued

| Date | Dose | Temp | pH | SG | CR | bar | u | p | $nu_p$ |
|---|---|---|---|---|---|---|---|---|---|
| 05-06-91M | 40 | N/T | 5.40 | 1.019 | N/T | N/T | 174 | 5 | LOW |
| 05-03-91F | 40 | N/T | 5.40 | 1.009 | 89 | HI | 296 | 26 | 1389 |
| | | | | Mean: | 141 | | 1456 | 52 | 1709 |
| | | | | SD: | 49 | | 1661 | 32 | 769 |
| | | | | CV: | 35.0 | | 114 | 62.3 | 45 |
| | | | | Tests: | 12 | | 12 | 12 | 12 |

TABLE D

| Date | Dose | Temp | pH | SG | CR | bar | u | p | $nu_p$ |
|---|---|---|---|---|---|---|---|---|---|
| 04-04-92S | 130 | 95.0 | 5.80 | 1.013 | 196 | 0 | 4915 | 373 | 7728 |
| 03-28-92S | 130 | 98.0 | 5.90 | 1.020 | 210 | 0 | 6565 | 287 | 5944 |
| 03-21-92S | 110 | 95.0 | 5.50 | 1.021 | 216 | 0 | 9651 | 278 | 6580 |
| 03-14-92S | 110 | 97.0 | 5.70 | 1.022 | 210 | 0 | 8964 | 282 | 6703 |
| 03-07-92S | 110 | 96.0 | 6.30 | 1.014 | 186 | 0 | 4471 | 395 | 10880 |
| 03-02-92M | 110 | 95.0 | 5.60 | 1.022 | 206 | 0 | 8778 | 254 | 6025 |
| 02-21-92F | 120 | 96.0 | 6.20 | 1.016 | 181 | 0 | 5169 | 403 | 8970 |
| 02-15-92S | 120 | 98.0 | 5.90 | 1.015 | 187 | 0 | 4525 | 306 | 6778 |
| 02-08-92S | 120 | 96.0 | 6.10 | 1.017 | 181 | 0 | 5506 | 364 | 8074 |
| 01-31-92F | 120 | 95.0 | 6.20 | 1.016 | 218 | 0 | 6896 | 425 | 11966 |
| 01-18-92S | 120 | 96.0 | 5.50 | 1.021 | 224 | 0 | 9503 | 274 | 6031 |
| 01-11-92S | 130 | 96.0 | 5.30 | 1.020 | 182 | 0 | 9494 | 249 | 5117 |
| | | | | Mean: | 200 | 0 | 7036 | 324 | 7236 |
| | | | | SD: | 16 | 0 | 2114 | 63 | 1467 |
| | | | | CV: | 8.0 | 0 | 30 | 19.5 | 20.2 |
| | | | | Tests: | 12 | 12 | 12 | 12 | 12 |

Case #3

Shown in Table E are examples of estimated plasma methadone levels for four patients demonstrating how to detect misuse of methadone.

TABLE E

Utilization of Plasma Methadone Levels
To Uncover Misuse of Methadone
Estimated Plasma Methadone Concentration (ng/ml), p

| Sample | Patient A* | Patient B | Patient C*** | Patient D |
|---|---|---|---|---|
| 1 | 480 | 346 | 89 | 1247**** |
| 2 | 465 | 234 | 44 | 1173**** |
| 3 | 485 | 281 | 50 | 1061**** |
| 4 | 525 | 233 | 334 | 1343**** |
| 5 | 454 | 376 | 84 | 435 |
| 6 | 410 | 208 | 310 | 575 |
| 7 | 531 | 290 | 778 | 427 |
| 8 | 483 | 172** | 8.00 | 514 |
| 9 | 403 | 0** | 33 | 474 |

*Patient A ingests 90 mg/day of methadone q24 hr. as instructed. He ingests a does in the clinic on Mon., Wed. and Fri., mean 24-hr. trough level is 470 ng/ml with a CV = 9.4%.
**Patient B receives 80 mg/day of methadone. She only gets a take home dose for Sunday. Expected mean value (samples 1–6) is 281 +/− 62 ng/ml. Sample 8 was taken 48 hr. after her last dose providing an estimate of plasma methadone half-life of about 65 hrs. Sample 9 is an example of substitution on a non-patient urine sample.
***Patient C ingests 50 mg/day in clinic on Mon., Wed. and Fri. Her expected plasma methadone concentration should be about 170 ng/ml. She is likely diverting Tues, Thur. and Sun. take home doses and spiking urines with exogenous methadone on other days. Solution was to withdraw take home doses.
****Patient D currently ingests 100 mg/day of methadone (samples 5–9). Previously, he was ingesting over 200 mg/day of methadone via supplementing with illicit methadone (samples 1–4). Solution was to slowly taper him back to 100 mg/day on a daily basis of clinic visits.

Cases #4 and #5

Shown in Tables F and G are data demonstrating how the statistical program is utilized by the computer to 'flag' a urine methadone value as being outside the acceptable range for the patient. With this data it is possible for a healthcare provider to speak with a patient about this abnormality before it becomes a continuing problem. Typically, lab errors are ruled out prior to discussion with the patient. Assuming no laboratory explanation is forthcoming, the healthcare provider can consider substitution of urine by the patient (often noted by variation in measured urinary parameters, including normalized creatine); ingestion of methadone on a non-24 hour basis; ingestion of additional and unapproved methadone; selling of take-home methadone doses; taking a medication interfering with the metabolism of methadone and so forth. Having an objective and quantitative methadone history to present to the patient overcomes the natural tendency for many patients to be untruthful.

TABLE F

| Date | Dose | Temp | pH | SC | CR | u | p | nu$_p$ | Pred |
|---|---|---|---|---|---|---|---|---|---|
| 09-10-93F | 140 | 95.0 | 7.11 | 1.013 | 307 | 3631 | 352 | 17072 | High |
| 09-08-93W | 140 | 95.0 | 5.19 | 1.025 | 306 | 12847 | 204 | 4686 | |
| 09-02-93h | 140 | 95.0 | 5.49 | 1.023 | 317 | 6345 | 154 | 3555 | |
| 08-30-93M | 140 | 95.0 | 4.68 | 1.023 | 316 | 12629 | 144 | 3269 | |
| 08-26-93h | 140 | 95.0 | 4.91 | 1.020 | 224 | 10227 | 186 | 4251 | |
| 08-23-93M | 120 | 94.0 | 4.91 | 1.025 | 239 | 14105 | 172 | 4466 | |
| 08-20-93F | 120 | 94.0 | 5.78 | 1.028 | 299 | 8194 | 172 | 4511 | |
| 08-17-93T | 120 | 94.0 | 5.31 | 1.026 | 311 | 8814 | 145 | 3768 | |
| 08-13-93F | 120 | 94.0 | 6.18 | 1.013 | 357 | 3101 | 314 | 8401 | |
| 08-10-93T | 120 | 95.0 | 5.81 | 1.021 | 296 | 4634 | 173 | 4550 | |
| 08-06-93F | 120 | 95.0 | 6.69 | 1.019 | 243 | 2923 | 252 | 6696 | |
| 08-03-93T | 120 | 95.0 | 5.53 | 1.024 | 185 | 8645 | 201 | 5264 | |
| | | | Mean: | 283 | 8008 | 206 | 5130 | | |
| | | | SD: | 49 | 3945 | 67 | 1710 | | |
| | | | CV: | 17.3 | 49.2 | 32.4 | 33.3 | | |
| | | | Tests: | 12 | 12 | 12 | 11 | | |

TABLE G

| Date | Dose | Temp | pH | SC | CR | u | p | nu$_p$ | Pred |
|---|---|---|---|---|---|---|---|---|---|
| 08-06-93F | 130 | 96.0 | 4.88 | 1.025 | 49L | 4305 | 97 | 1858 | LOW |
| 08-02-93M | 130 | 96.0 | 4.81 | 1.024 | 215 | 13601 | 163 | 5922 | |
| 07-29-93h | 130 | 96.0 | 5.05 | 1.019 | 211 | 11105 | 249 | 9089 | |
| 07-26-93M | 130 | 95.0 | LOW | 1.014 | 214 | 8822 | 163 | 5865 | |
| 07-22-93h | 130 | 96.0 | 4.52 | 1.028 | 42L | 4431 | 98 | 1042 | LOW |
| 07-19-93M | 130 | 95.0 | 4.66 | 1.021 | 258 | 25400 | 333 | 12050 | |
| 07-15-93h | 130 | 96.0 | 5.96 | 1.003 | LOW | 5585 | 381 | 97615 | HIGH |
| 07-12-93m | 130 | 96.0 | 4.76 | 1.021 | 228 | 14361 | 208 | 7550 | |
| 07-09-93F | 130 | 94.0 | 4.76 | 1.015 | 230 | 10940 | 266 | 9563 | |
| 07-06-93T | 130 | 96.0 | 5.20 | 1.024 | 249 | 17816 | 309 | 11313 | |
| 07-01-93h | 130 | 96.0 | 5.10 | 1.012 | 224 | 6963 | 319 | 11630 | |
| 06-28-93M | 130 | 97.0 | LOW | 1.011 | 241 | 7478 | 190 | 6841 | |
| 06-24-93h | 130 | N/T | LOW | 1.009 | 232 | 6889 | 224 | 8088 | |
| | | | Mean: | 214 | 10585 | 231 | 8396 | | |
| | | | SD: | 41 | 6037 | 89 | 3288 | | |
| | | | CV: | 19.1 | 57 | 38.5 | 39.1 | | |
| | | | Tests: | 12 | 13 | 13 | 13 | | |

Case #6

Figure 8:
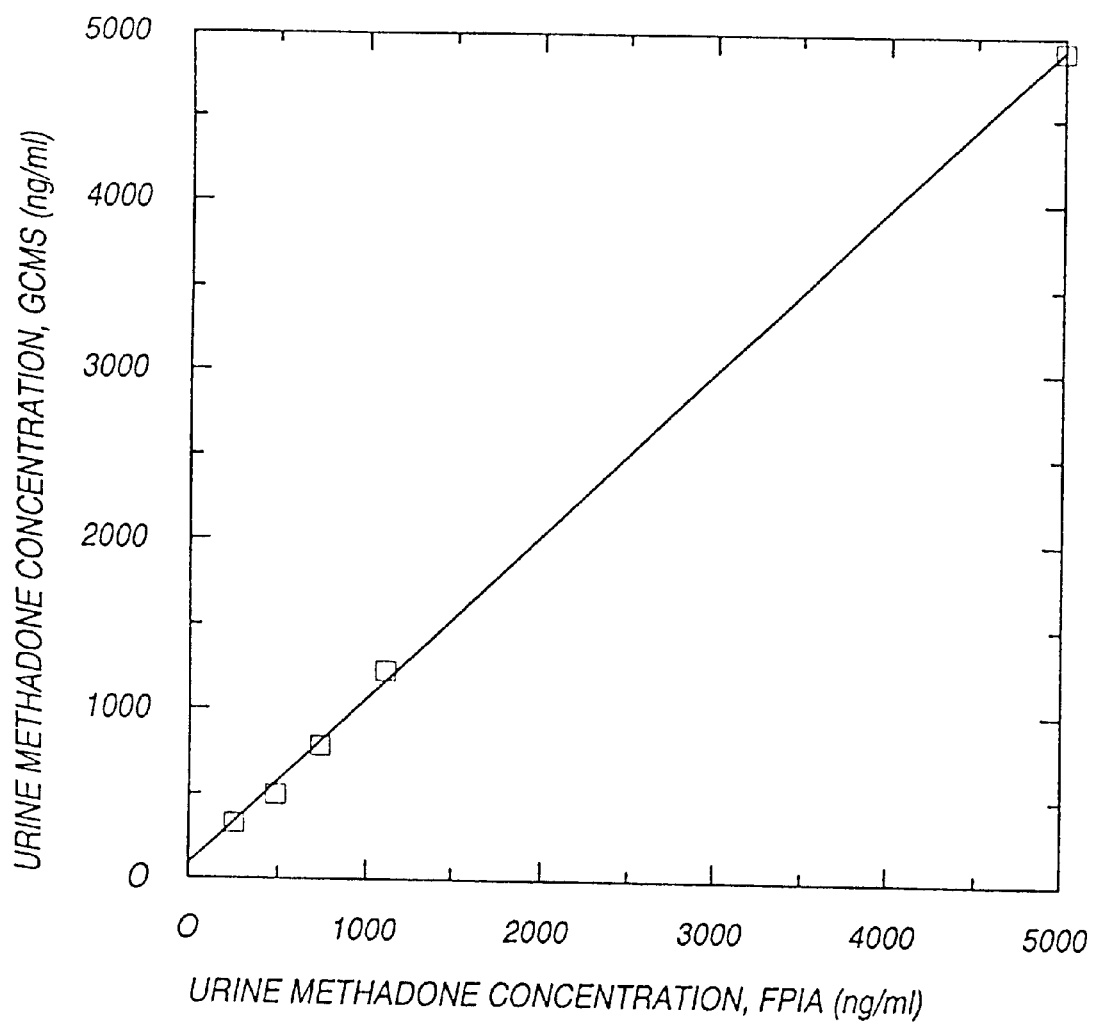
FIG. 8 is a graph of urine methadone concentrations simultaneously measured by FPIA and gas chromatography/mass spectrometry (GC/MS).

Methadone concentration data were simultaneously measured using GC/MS and FPIA for urine obtained from five patients and plotted in FIG. 8 for comparison. Linear regression analysis shows that GCMS=0.97*FPIA=48, R=0.999: both methods are essentially equivalent. Similarly, methods other than GC/MS or FPIA could also be used, such as gas chromatography, high pressure liquid chromatography, chemical methods and so on, to sequentially follow raw urine methadone concentration patient data for utilization in this invention.

MEDICATION MAINTENANCE PROGRAMS

A patient is initially prescribed a medication and dose based on several factors. These ordinarily include the severity and duration of illness, amounts and types of medications previously used, current or previous physiological and/or physical dependence upon other prescription or illicit drugs, previous medical history, patient sex, pregnancy status, patient weight and ingestion of other therapeutic medications. Normally medication dose is adjusted upwardly until a patient no longer complains of residual signs and symptoms of his or her psychiatric and/or medical illness, is no longer experiencing withdrawal signs and symptoms if on a medication-replacement taper to abstinence program, or loses his or her desire to use illicit medications if a substance abuse problem exists. Medication dose is increased per published and accepted standard medical protocols for each family of psychiatric and medical drug, usually "x" mg every few days.

Figure 9:
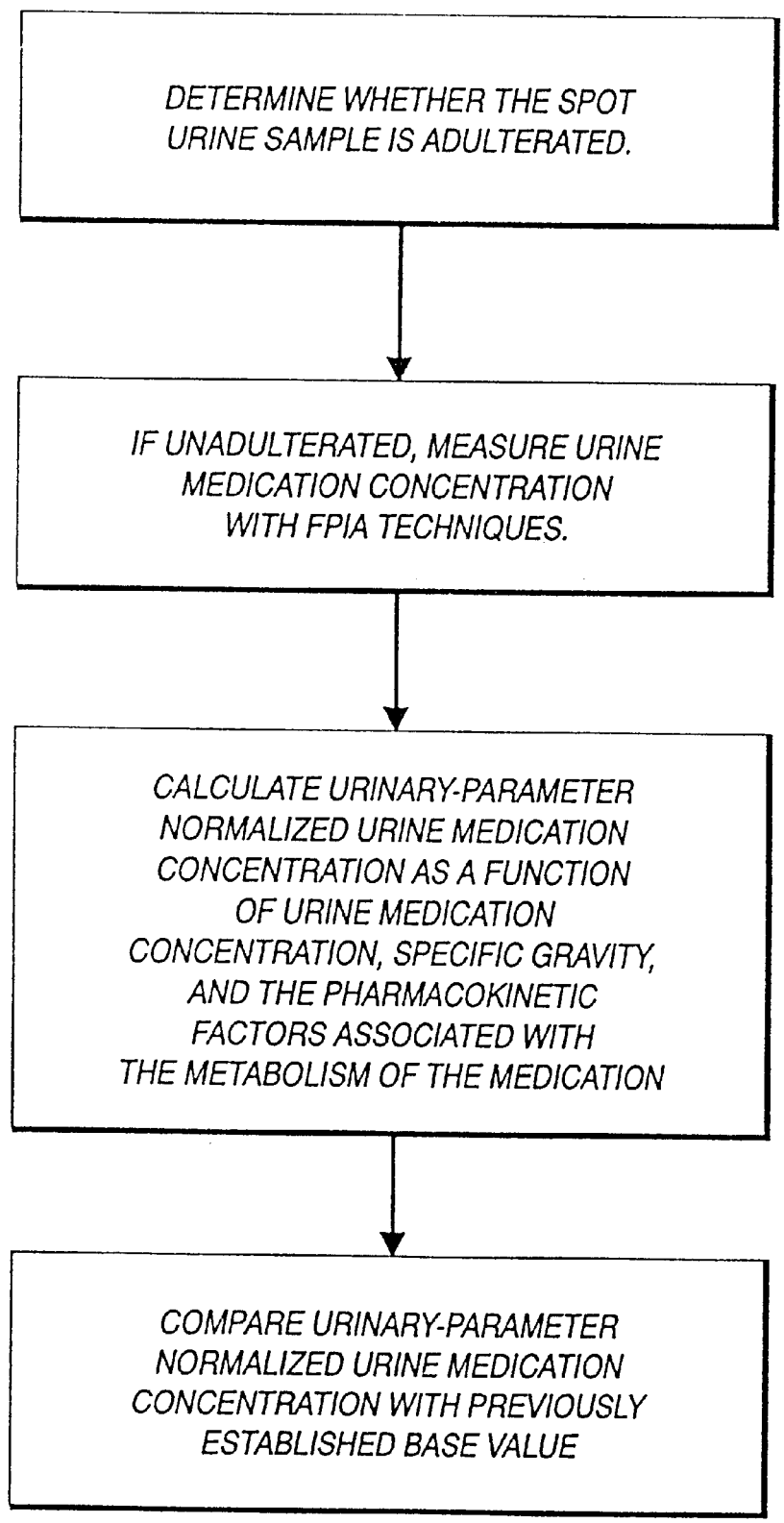
FIG. 9 is a block diagram of a preferred method of the present invention as it relates to monitoring medication maintenance programs.

To determine compliance with the prescribed medication dose, random urine samples are obtained from the patient and analyzed in accordance with the invention as described in FIG. 9. If tested and determined to be unadulterated, a raw urine parent drug and/or its metabolites concentration is measured preferably using FPIA. Metabolites are those substances which result from the body's metabolism of the parent drug. The metabolites are detectable and part of the value obtained when measuring the raw urine medication concentration. The raw urine medication concentration (u) is next converted to a normalized urine medication concentration (nu) as discussed below. Over time, a normalized urine medication concentration-daily medication dose relationship is derived for each individual patient, which can be compared to the relationship expected for that particular patient. Alternatively, by adjusting the normalized urine medication concentration relative to the urinary pharmacokinetic parameters for each medication, a urinary-parameter normalized urine medication concentration (nu$_p$) may be calculated and compared to that expected for an average patient to determine compliance with the patient's prescribe medication dose.

Again, if the relationships between the present nu and the expected nu are not similar, either the patient's metabolism rate is causing an over- or under-effectiveness of the prescribed dose or the patient is not complying with his or her prescribed dose. If related to the patient's individual metabolism rate, a physician can now optimize the patient's medication dose to achieve an efficacious and safe plasma medication concentration. Once the optimum medication dose is established for the patient, a physician can monitor the patient for compliance with his or her prescribed dose by comparing either the nu or the $nu_p$ with their expected values for the particular medication dose; hence, uncovering covert medication diversion or supplementing.

The steps of testing for adultration of the urine sample and determination of the raw urine medication concentration are also utilized in determining compliance with a medication maintanence program and follow the same procedures as discussed above in methadone maintanence programs.

Determination of Normalized Urine Medication Concentration

The normalized urine medication concentration, nu, is statistically constant for each patient relative to the medication dose regardless of an individual's medication metabolism (if the immunoreactivity for the FPIA antibody is nonselective between parent and drug metabolites) and daily changes in urine parameters. In determining how to calculate nu, the linear relationship developed above between the urine volume production rate factor (UVPRF) and the reverse urine creatinine excretion factor (RUCEF) was utilized. This relationship, as shown in FIG. 4, is represented as follows:

$$RUCEF=0.942(SE\ 0.013)\cdot UVPRF+0.121(SE\ 0.043) \quad (13)$$

$$u'/u=0.942\cdot v/v'+0.121 \quad (14)$$

Therefore, contrary to the traditional teachings of those skilled in the art, urine drug and metabolite concentrations, u, are inversely related to the volume, v, of urine produced by the kidneys.

Following the same logic in determining plasma methadone concentration equation, the standard dimensionally correct renal clearance equation is utilized, which is $$cl=(u\cdot v)/p \quad (15)$$

Assuming that at steady-state plasma medication concentration and renal clearance are constant, the product $(u\cdot v)$ must also be constant at any particular time point. It follows that an empirical mathematical relationship exists between u and v such that given an arbitrary urine volume production rate v' and an equivalent u' at a reference point (specific gravity 1.030):

$$\{u\cdot v\}_{sg\ actual}=\{u'\cdot v'\}_{sg\ 1.030} \quad (16)$$

or upon rearrangement for u' gives, $$u'=u\cdot(v/v') \quad (17)$$

where the products given in Equations (16) and (17) are those measured for a spot urine collected with an actual specific gravity (u,v) and a corrected specific gravity typical of a morning void of 1.030 (u',v'). Utilizing the linear relationship that exists between urine volume production rate factor (UVPRF) and the specific gravity factor (SGF) in Equation (10) and combining it with Equation (17), a normalized urine medication concentrations can be calculated as follows:

$$nu=u'=u\cdot(v/v')=u\cdot UVPRF=u\cdot(k_1\cdot SGF-k_2) \quad (18)$$

wherein $k_1$ is a constant equal to 2.43 and $k_2$ is a constant equal to 1.43.

Determination of Urinary-Parameter Normalized Urine Concentration

The parameters of a patient's urine vary from one day to the next dependant upon the type and quantities of foods and beverages ingested. Additionally, individuals metabolize these substances, as well as medication, at different rates. By adjusting the normalized urine medication concentration to account for these variations, the urinary-parameter normalized urine medication concentration ($nu_p$) is calculated. Use of the $nu_p$ is preferable in the clinical setting because $nu_p$ is an alteration based on pharmacokinetic parameters important for a particular drug or family of drugs, thus providing a value that may be compared to that expected of the average patient.

Some important pharmacokinetic parameters include: patient body weight, whether a drug is a weak acid or weak base, how a drug is absorbed into tissues and blood, how the drug is administered (ie., orally, intravenously), whether a drug is a controlled release formulation, how a drug distributes in the body (patient volume of distribution, protein binding, tissue binding, lipidicity, redistribution), whether biotransformation occurs (cross-reactive metabolites, chemical half-life, tissue half-life), how the drug is excreted (renal clearance, hepatic clearance, tissue clearance, fecal clearance, dosing rate and amount, final steady-state concentrations of peak and trough levels of drug, zero order, first order or mixed order biotransformation reaction). These parameters may be measured by utilizing readily available values such as patient body weight, prescribed medication dose, urine pH, and urine volume production rate. For example, pH is an important variable if one is monitoring weak bases such as methadone, but is of only minor importance when monitoring weak acids such as the glucuronide derivatives of benzodiazepines and opioids. The pharmacokinetic parameters for each drug are available in medical references such as Goodman & Gillman, *The Pharmacological Basis of Therapeutics,* 8th Edition, Pergamon Press, 1990.

The relationships for any medication family between nu and the medication pharmacokinetic parameters are empirically developed using regression analysis. For example, in the case of diazepam and alprazolam, urine pH is not important. However, the following equation linearly adjusts each patient value to a standard weight of 70 kg (154 lb) for useful results:

$$nu_p(\text{patient body weight}/k_3)\cdot u\cdot UVPRF \quad (19)$$

wherein $k_3$ is a constant equal to 70. This value, once accurately established for a patient within a statistical margin of error, is used to evaluate medication diversion or supplementation in the patient by comparing subsequent calculations of this value with that an expected value of the average patient. If the subsequent calculation is similar to the expected value, the patient is complying with his prescribed dose.

Statistical methods similar to those proposed for methadone can be used to establish confidence limits.

Determining Daily Medication Dose Ingested

Figure 10:
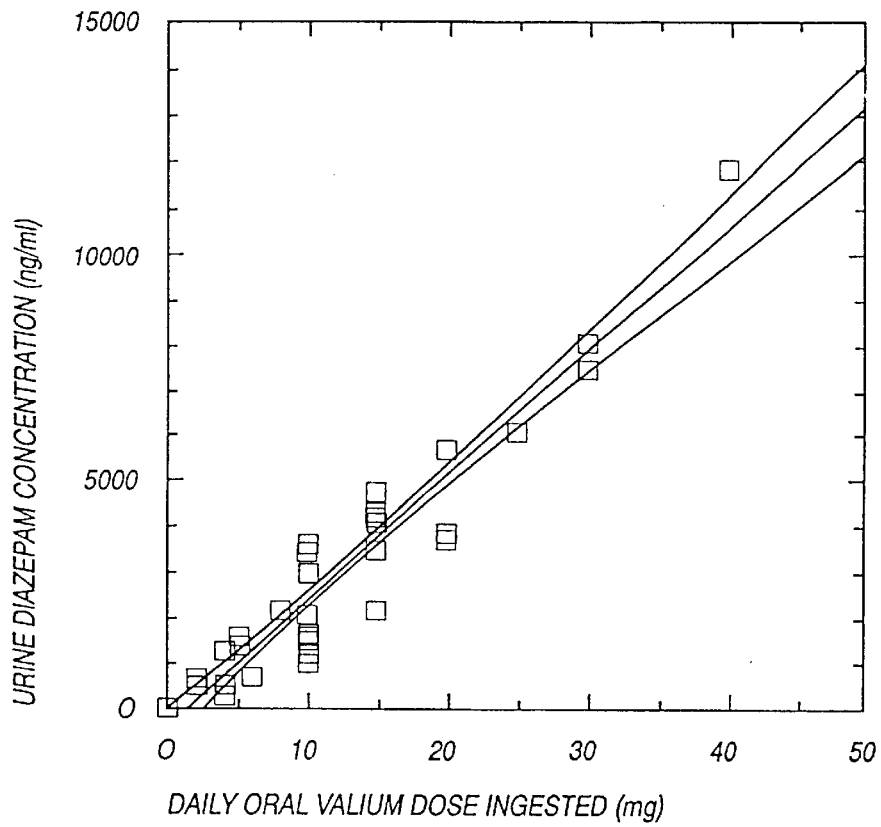
FIG. 10 is a graph of urinary-parameter normalized urine diazepam concentration versus daily oral valium dose ingested.
Figure 11:
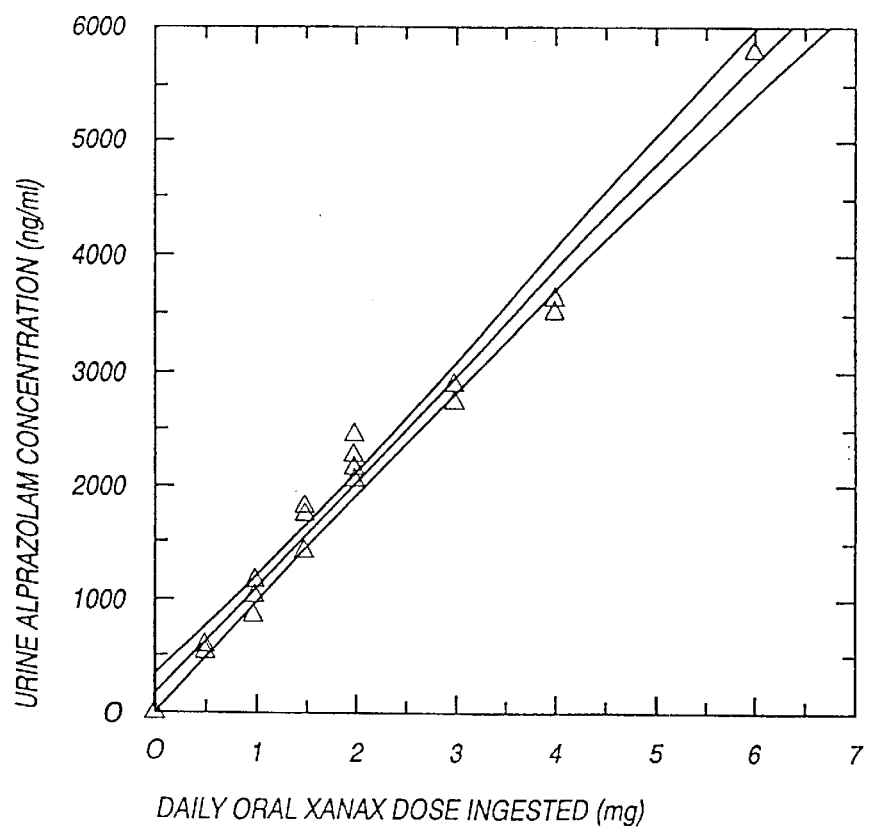
FIG. 11 is a graph of urinary-parameter normalized urine alprazolam concentration versus daily oral xanax dose ingested.

Once the urinary-parameter normalized urine medication concentration is calculated from Equation (19), it and the patient's daily medication dose are compared to that expected from a standard population. FIGS. 10 and 11 show how urinary-parameter normalized urine medication concentration varies with dose for patients prescribed and properly ingesting diazepam and alprazolam. Using these graphs, a clinician can estimate how a change of dose will effect the patient's urine medication concentration. If a patient's urinary-parameter normalized urine medication concentration is less than that expected from FIGS. 10 or 11, such a result may indicate that the patient is diverting the medication to others or simply not using it. Higher concentrations per dose suggest the opposite of the above.

Figure 12:
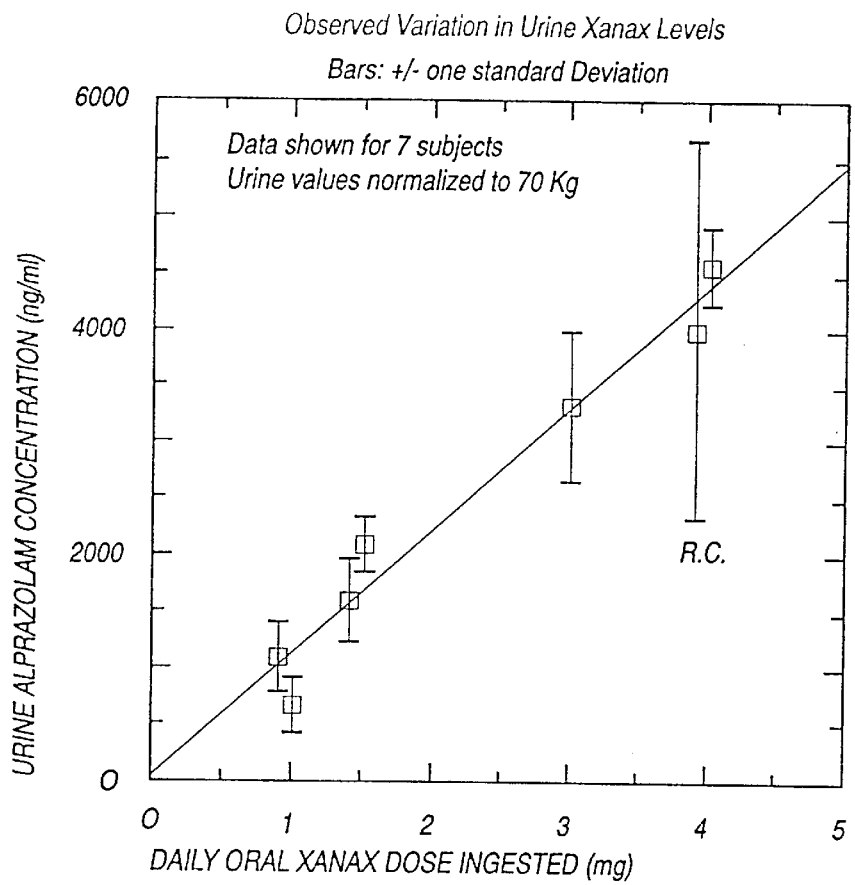
FIG. 12 is a graph of urinary-parameter normalized urine alprazolam concentration versus daily oral xanax dose ingested showing patient standard deviations and mean levels.

A further appreciation for consistency of medication ingestion by patients is shown in FIG. 12. The mean alprazolam normalized concentrations and standard deviations for several patients are plotted. As is apparent, all patients except one had SD of about +/−15% of the mean. The lone patient with a much higher variation was found to be ingesting on average 4 mg alprazolam per day, ranging from 2 to 8 mg per day.

In general, it has been determined that most patients ingesting proper, prescribed dosages of medications produce a point-of-time, spot $nu_p$ value that is often within +/−20% of their individual mean value for any particular medication and dose. Although, actual acceptance values must be determined for each medication and assay method.

Two methods of interpreting urine medication results for compliance monitoring have now been developed. The first and most primitive method is to simply establish, using data from controls and compliant patients, mean drug levels and the expected ranges (minimums and maximums) for the $nu_p$ of each particular medication at each particular daily, total dose amount. For example, it has been determined that the following equations for estimating the expected mean medication concentrations as a function of total, daily medication dose are useful for monitoring the benzodiazepine parent drugs and metabolites using FPIA (temazepam, clonidine, flurazepam and oxazepam are similar to diazepam):

$$\text{Alprazolam}: nu_p = 910(\text{SE } 31.4)*\text{Dose, SEE } 210 \quad (20)$$

$$\text{Diazepam}: nu_p = 267(\text{SE } 16.9)*\text{Dose, SEE } 806 \quad (21)$$

Acceptable maximum and minimum ranges of the $nu_p$ calculated by Equation (19) for any patient (after ruling out metabolic problems) are simply given as +/−20% of the expected mean value of $nu_p$ at any dose for a compliant patient as calculated by Equation (20) or (21).

A second and more sophisticated method for evaluating individual normalized medication concentrations for a spot urine sample utilizes probability theory and prediction intervals. To use this method, one calculates mean and SD for each control and patient sample set and plots the SD for each subject versus size of each subject's sample set. Using standard prediction formulas and confidence limits on the population of SD, one estimates from the actual data (each drug and drug family is unique) the true standard deviation for the population of all persons ingesting the drug properly. Given this value for the true population SD, other prediction equations can be derived of the form, acceptable value= patient mean +/−x·SD, where x is a factor whose value is dependent upon sample size and desired confidence limit, eg, 95, 97.5, 99, and 99.999%. Once these values have been determined, the urinary-parameter normalized urine concentration calculated by Equation (19) can be compared to an expected range and noted as low, acceptable or high.

Given sufficient control and patient data and a method of analysis, preferably though not limited to quantitative immunoassay like FPIA, similar relationships for mean urinary-parameter normalized urine medication concentrations as a functions of daily medication dose can easily be derived both for other drugs in the benzodiazepine family and for other distinctly different chemical families, making this method broadly useful. Therefore, this method is useful not only for determining the average amounts of medication taken each day, but how irregular the patient may be from one day to another.

Clinical Examples

Case #6

J. W. is a 34 year old male presented for treatment of an anxiety disorder. He had been ingesting 1.5 mg alprazolam daily. After placing the patient into an individualized, anxiety-reduction therapy program, his psychiatrist was able to gradually decrease his alprazolam to abstinence. The patient later attended college without evidence of return to medication use. Shown in Table H is a partial representation of a standard computer printout for this compliant patient who was slowly tapered from alprazolam using the $nu_p$ method as an aid to downward dose adjustments. The last column in the figure marked BENZ represents $nu_p$ values for the patient which are quite constant once specific gravity and patient weight corrections are made to the raw urine medication concentration (u).

TABLE H

| Date | Temp | pH | SG | CR | $nu_p$, Ben |
|---|---|---|---|---|---|
| 09-28-92M | 98.0 | 5.40 | 1.024 | 253 | 280 |
| 09-22-92T | 98.0 | 5.70 | 1.028 | 235 | 182 |
| 09-21-92M | 96.0 | 5.10 | 1.025 | 279 | 228 |
| 09-17-92h | 96.0 | 5.60 | 1.029 | 248 | 168 |
| 09-16-92W | 98.0 | 5.30 | 1.028 | 199L | 168 |
| 08-27-92h | 98.0 | 5.40 | 1.025 | 234 | 184 |
| 08-24-f92M | 98.0 | 5.50 | 1.029 | 289 | 162 |
| | | | Mean: | 257 | 196 |
| | | | SD: | 48 | 44 |
| | | | CV: | 9.6 | 21.9 |
| | | | Tests: | 12 | 7 |
| 08-14-92F | 97.0 | 5.40 | 1.027 | 271 | 260 |
| 08-10-92M | 97.0 | 5.40 | 1.029 | 260 | 388 |
| 08-06-92h | 98.0 | 5.30 | 1.028 | 242 | 352 |
| 08-05-92W | 98.0 | 5.80 | 1.029 | 234 | 306 |
| 07-29-92W | 97.0 | 5.40 | 1.028 | 202L | 252 |
| 07-27-92M | 96.0 | 5.30 | 1.024 | 271 | 420 |
| 07-24-92F | 98.0 | 5.70 | 1.024 | 244 | 522 |
| 07-20-92M | 98.0 | 7.20 | 1.022 | 315 | 662 |
| 07-17-92F | 97.0 | 6.60 | 1.029 | 219 | 426 |
| 07-15-92W | 97.0 | 5.90 | 1.021 | 271 | 634 |
| | | | Mean: | 254 | 422 |
| | | | SD: | 28 | 144 |
| | | | CV: | 11.1 | 34.1 |
| | | | Tests: | 12 | 10 |
| 06-01-92M | 97.0 | 5.80 | 1.030 | 286 | 718 |
| 05-27-92W | 97.0 | 5.40 | 1.013 | 267 | 1032 |
| 05-26-92T | 94.0 | 5.60 | 1.030 | 283 | 720 |
| 05-21-92h | 98.0 | 6.00 | 1.021 | 286 | 830 |
| 05-19-92T | 96.0 | 5.70 | 1.023 | 278 | 948 |
| 05-13-92W | 98.0 | 5.60 | 1.029 | 241 | 670 |
| 05-09-92S | 96.0 | 6.40 | 1.023 | 269 | 784 |
| 05-05-92T | 96.0 | 5.50 | 1.018 | 284 | 1098 |
| 05-04-92M | 98.0 | 5.70 | 1.027 | 256 | 840 |
| 04-30-92h | 95.0 | 5.80 | HI | 277 | 940 |
| 04-27-92M | 96.0 | 5.40 | 1.011 | 288 | 1200 |
| 04-24-92F | 96.0 | 5.50 | HI | 277 | 826 |
| | | | Mean: | 274 | 884 |
| | | | SD: | 14 | 164 |

TABLE H-continued

| Date | Temp | pH | SG | CR | $nu_p$, Ben |
|---|---|---|---|---|---|
| | | | CV: | 5.1 | 18.4 |
| | | | Tests: | 12 | 12 |
| 04-20-92M | 98.0 | 5.40 | 1.022 | 335 | 1164 |
| 04-15-92W | 96.0 | 5.70 | 1.024 | 268 | 1014 |
| 04-13-92M | 96.0 | 5.90 | 1.019 | 271 | 1174 |
| 04-10-92F | 98.0 | 5.70 | 1.021 | 377H | 1246 |
| 04-06-92M | 98.0 | 5.90 | 1.028 | 261 | 858 |
| 04-02-92h | 96.0 | 5.70 | 1.025 | 271 | 1052 |
| 03-30-92M | 94.0 | 5.60 | 1.021 | 303 | 1512 |
| 03-25-92W | 98.0 | 5.20 | 1.021 | 271 | 1346 |
| 03-24-92T | 98.0 | 6.00 | 1.023 | 243 | 1330 |
| 03-20-92F | 96.0 | 5.80 | 1.024 | 272 | 1278 |
| 03-16-92M | 94.0 | 5.30 | 1.022 | 286 | 1464 |
| 03-13-92F | 96.0 | 5.70 | 1.019 | 277 | 1710 |
| | | | Mean: | 285 | 1262 |
| | | | SD: | 32 | 234 |
| | | | CV: | 11.2 | 18.5 |
| | | | Tests: | 12 | 12 |

Case #7

R. C. is a 38 year old long-term opiate addict who was prescribed alprazolam by an outside psychiatrist. This patient's drug use was monitored to insure that he was compliant with his prescription. Data for this patient is shown in FIG. 12 and Table I. Table I is the urine data sheet demonstrating large variation in the BENZ levels consistent with irregular ingestion of alprazolam. FIG. 12 shows the elevated SD measured for this non-compliant patient as compared to others.

TABLE I

| Date | Dose | pH | SG | Ben |
|---|---|---|---|---|
| 04-05-90 | 0 | 5.0 | 1.016 | 2896** |
| 04-13-90 | 80 | 5.5 | 1.018 | 6128** |
| 04-16-90 | 80 | 8.0 | 1.005 | 6252** |
| 04-23-90 | 80 | 5.5 | 1.010 | 3358** |
| 04-30-90 | 80 | 5.5 | 1.000 | 4110** |
| 05-18-90 | 90 | 5.5 | 1.008 | 3322** |
| 06-01-90 | 90 | 5.5 | 1.013 | 1512** |
| 06-04-90 | 90 | 5.1 | 1.015 | 1790** |
| 06-11-90 | 90 | 5.0 | 1.001 | 2468** |
| 06-18-90 | 90 | 5.6 | 1.006 | 1836** |
| 06-29-90 | 90 | 5.0 | 1.005 | 2664** |
| 07-13-90 | 90 | 6.1 | 1.016 | 684** |
| 07-16-90 | 90 | 5.5 | 1.001 | 0 |
| 07-27-90 | 90 | 5.1 | 1.006 | 3120** |
| 07-30-90 | 90 | 5.0 | 1.005 | 2932** |
| 08-06-90 | 90 | 5.5 | 1.015 | 2928** |
| 08-15-90 | 90 | 7.1 | 1.009 | 2648** |
| 08-20-90 | 90 | 5.0 | 1.018 | 2502** |
| 08-29-90 | 90 | 5.6 | 1.016 | 2860** |
| 09-04-90 | 90 | 6.5 | 1.025 | HI** |
| 09-05-90 | 90 | 6.1 | 1.019 | 3468** |
| 09-10-90 | 90 | 5.0 | 1.013 | 4194** |
| 09-24-90 | 90 | 7.0 | 1.005 | 4962** |
| 10-01-90 | 90 | 5.0 | 1.010 | 6552** |
| 10-02-90 | 90 | 6.1 | 1.010 | 2816** |
| 10-08-90 | 90 | 5.1 | 1.023 | 2510** |

***Xanax level: mean = 4268 ng/ml, CV = 49.8% (normalized to 70 kg)

Case #8

A. S. is a 42 year old female requiring treatment of severe, episodic pain associated with spasm of the levator ani muscle of the pelvic floor. She was prescribed Tylenol #3 (30 mg of codeine) po q8h for relief of severe pain, prescribed Norflex 100 mg po bid to help relieve referred spasms of the buttock area and entered into a Rolfing program to realign her axial skeleton and balance the pelvic musculature. Following the above treatment plan her problem resolved over a 6 month period allowing discontinuation of all medications other than occasional Norflex.

Figure 13:
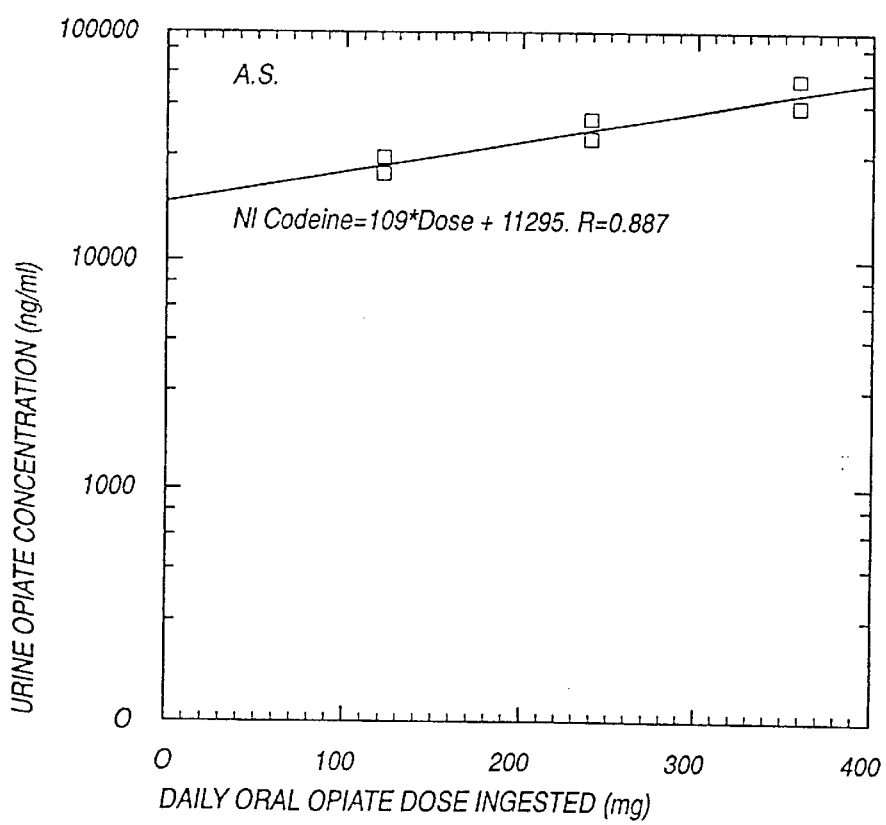
FIG. 13 is a graph of urinary-parameter normalized urine opiate concentration for codeine versus daily oral medication dose ingested.

Shown in FIG. 13 are mean $nu_p$ values for codeine as a function of daily, total dose. Although the numbers are different, results are qualitatively similar to those seen with the benzodiazepines and methadone. Her mean codeine level while stabilized on 90 mg of codeine qd, as shown on FIG. 13, should be 19,102 +/−3840 ng/ml. A summary of her weekly urine test results are also shown in Table J.

TABLE J

| Date | Dose | Temp | pH | SG | CR | Coc | Opi |
|---|---|---|---|---|---|---|---|
| 09-10-93F | 9-0 | 94.0 | LOW | 1.013 | 42L | | 20471 |
| 09-03-93F | 9-0 | 95.0 | 5.60 | 1.017 | 343 | | 15492 |
| 08-27-93F | 9-0 | 94.0 | 5.62 | 1.014 | 292 | | 18659 |
| 08-18-93W | 9-0 | 96.0 | 5.50 | 1.022 | 355 | 0 | 21775 |
| 08-03-93T | 9-0 | 92.0 | 4.72 | 1.010 | 372 | | 13830 |
| 07-30-93F | 9-0 | 94.0 | 5.53 | 1.023 | 390 | | 20457 |
| 07-16-93F | 9-0 | N/T | 5.83 | 1.015 | 347 | 0 | 25039 |
| 06-28-93M | 9-0 | 96.0 | 6.10 | 1.017 | 383 | | 21894 |
| 06-18-93F | 9-0 | 95.0 | 5.90 | 1.019 | 368 | | 14297 |
| | | | | Mean: | 349 | | 19102 |
| | | | | SD: | 34 | | 3840 |
| | | | | CV: | 9.5 | | 20.1 |
| | | | | Tests | 9 | | 9 |

Case #9

W. K. is a 44 year old male requiring opioid medications for severe arachnoiditis following surgery in the lumber spine. He was prescribed oxycodone without acetaminophen since he is status post removal of one kidney because of renal carcinoma. Shown in Table K are his oxycodone levels (40 mg per day total dose) which are within acceptable limits of 800–1600 ng/ml.

TABLE K

| Date | Temp | pH | SG | CR | $nu_p$, Opi |
|---|---|---|---|---|---|
| 02-14-94M | 98.0 | 5.25 | 1.010 | 446H | 1530 Rx |
| 02-10-94h | 96.0 | 5.11 | 1.024 | 302 | 791 Rx |
| 02-07-94M | 94.0 | 5.20 | 1.015 | 359 | 1154 Rx |
| 02-03-94M | 96.0 | 5.33 | 1.011 | 186L | 1062 Rx |
| 01-31-94M | N/T | 7.13 | 1.017 | 299 | 928 Rx |
| 01-27-94M | N/T | 5.21 | 1.013 | 286 | 583 Rx |
| 01-24-94M | N/T | 5.41 | 1.011 | 264 | 1305 Rx |
| 01-20-94M | N/T | 5.59 | 1.011 | 363 | 937 Rx |
| 01-17-94M | 94.0 | 5.76 | 1.010 | 447H | 1252 Rx |
| 01-13-94h | 95.0 | 5.51 | 1.009 | 309 | 1562 Rx |
| 01-10-94M | 94.0 | 5.44 | 1.012 | 415 | 1605 Rx |
| 01-06-94h | 94.0 | 6.12 | 1.004 | 223 | 1760 Rx |
| | | | Mean: | 324 | 1206 |
| | | | SD: | 79 | 362 |
| | | | CV: | 24.4 | 30.0 |
| | | | Tests: | 12 | 12 |

It is thus seen that methods are now provided that monitor patients who have been placed on medication maintenance programs for compliance without the need to draw blood. The invention utilizes readily obtainable urine medication concentrations from evaluation of patient urine samples by FPIA to determine normalized and urinary-parameter urine medication concentration, which can be respectively compared to historical patient data and general population data to confirm prescription compliance. Plasma medication concentrations may also be determined. The methods are clinically practical without high laboratory testing cost, the invasiveness of withdrawing blood, and the added exposure to medical professionals of patient blood having high probability of hepatitis and HIV infection.

While this invention has been described in detail with particular reference to preferred methods thereof, it should be understood that many modifications, additions and deletions may be made thereto without departure from the spirit and scope of the invention, including application to other drugs and medications, as set forth in the following claims.

I claim:

1. A method of monitoring compliance of a patient that has been placed on a medication maintenance program with a prescribed medication dosage, and with the method comprising the steps of
   (a) obtaining a sample of the patient's urine,
   (b) measuring the concentration of the medication or its metabolites in the urine and the urine specific gravity,
   (c) calculating a normalized urine medication concentration as the product of the measured medication concentration in the urine and a specific gravity factor, the specific gravity factor being a ratio of specific gravity of a typical morning void for the general population to the patient measured urine specific gravity, and
   (d) comparing the normalized urine medication concentration with an expected medication concentration value for the patient for the maintenance program prescribed to determine any significant differences therebetween as an indication of noncompliance.

2. The method of claim 1 wherein the specific gravity of a typical morning void for the general population has a value of 1.030.

3. A method of monitoring compliance of a patient that has been placed on a medication maintenance program with a prescribed medication dosage, and with the method comprising the steps of
   (a) obtaining a sample of the patient's urine,
   (b) measuring the concentration of the medication in the urine, the urine specific gravity and at least one selected pharmacokinetic parameter of the medication,
   (c) calculating a urinary-parameter normalized urine medication concentration as the product of the measured medication concentration in the urine, a specific gravity factor and the at least one selected pharmacokinetic parameter, the specific gravity factor being a ratio of specific gravity of a typical morning void for the general population to the patient measured urine specific gravity, and
   (d) comparing the urinary-parameter normalized urine medication concentration with an expected medication concentration value for an average compliant patient for the maintenance program prescribed to determine any significant differences therebetween as an indication of noncompliance.

4. The method of claim 3 wherein the specific gravity of a typical morning void for the general population has a value of 1.030.

5. A method of monitoring compliance of a patient that has been placed on a methadone maintenance program in accordance with claim 3 and wherein step (b) the concentration of methadone is measured.

6. The method of claim 5 wherein step (b) methadone dose, patient body weight and urine pH are measured as the selected pharmacokinetic parameters.

7. A method of monitoring compliance of a patient that has been placed on a methadone maintenance program which comprises the steps of
   (a) obtaining a sample of the patient's urine,
   (b) measuring the concentration of methadone, the specific gravity and the pH value of the urine sample,
   (c) calculating the concentration of methadone of the plasma as the product of the measured concentration of methadone of the urine, a specific gravity factor and urine pH, the specific gravity factor being a ratio of specific gravity of a typical morning void for the general population to the patient measured urine specific gravity, and
   (d) comparing the calculated concentration of methadone of the plasma with an expected value for the maintenance program prescribed.

8. The method of claim 7 wherein the specific gravity of a typical morning void for the general population has a value of 1.030.

* * * * *